(12) United States Patent
Schwartz et al.

(10) Patent No.: US 8,431,555 B2
(45) Date of Patent: Apr. 30, 2013

(54) TOPICAL STEROIDAL FORMULATIONS

(75) Inventors: Arthur G. Schwartz, Perkasie, PA (US); John R. Williams, Merion Station, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 675 days.

(21) Appl. No.: 12/494,928

(22) Filed: Jun. 30, 2009

(65) Prior Publication Data

US 2010/0004217 A1  Jan. 7, 2010

Related U.S. Application Data

(60) Provisional application No. 61/076,784, filed on Jun. 30, 2008.

(51) Int. Cl.
*A61K 31/56* (2006.01)

(52) U.S. Cl.
USPC .................................................. 514/177

(58) Field of Classification Search .......... 514/177
See application file for complete search history.

(56) References Cited

U.S. PATENT DOCUMENTS

| | | | |
|---|---|---|---|
| 4,898,694 A | 2/1990 | Schwartz et al. | |
| 5,001,119 A | 3/1991 | Schwartz et al. | |
| 5,028,631 A | 7/1991 | Schwartz et al. | |
| 5,157,031 A * | 10/1992 | Schwartz et al. | 514/177 |
| 5,714,481 A | 2/1998 | Schwartz et al. | |
| 5,744,462 A | 4/1998 | Schwartz et al. | |
| 7,271,234 B2 | 9/2007 | Kohn et al. | |
| 2003/0157157 A1 | 8/2003 | Luo et al. | |
| 2005/0020552 A1 * | 1/2005 | Aschkenasy et al. | 514/177 |
| 2007/0275936 A1 | 11/2007 | Ahlem et al. | |

OTHER PUBLICATIONS

Janjikhel, R., et al., "Improved Bioavailability of a Poorly Water Soluble Drug by Nanosizing," American Associattion of Pharmaceutical Scientists Journal, 4(S1), abstract only (2002).

Malik, A. S., et al., "A Novel Dehydroepiandrosterone Analog Improves Functional Recovery in a Rat Traumatic Brain Injury Model," Journal of Neurotrauma, 20(5): 463-477 (2003).
Nandi, I., et al., "Synergistic Effect of PEG-400 and Cyclodextrin to Enhance Solubility of Progesterone," AAPS PharmSciTech, 4(1): 1-5 (2003).
McCormick, D. L., et al., "Chemoprevention of rat prostate carcinogenesis by dietary 16α-fluoro-5-androsten-17-one (fluasterone), a minimally androgenic analog of dehydroepiandrosterone," Carcinogenesis, 28(2): 398-403 (2007).

* cited by examiner

*Primary Examiner* — Brandon Fetterolf
*Assistant Examiner* — Christopher R Stone
(74) *Attorney, Agent, or Firm* — Drinker Biddle & Reath LLP

(57) ABSTRACT

The present invention relates to formulations of poorly water soluble pharmaceutical agents of Formula I and II. The present invention also relates to compositions containing compounds of Formula I or II, and glucocorticoids, and methods for reducing side effects from glucocorticoid treatment by co-administration of compounds of Formula I and II. The compositions herein are useful for the treatment of diabetes and obesity related diseases including metabolic syndrome.

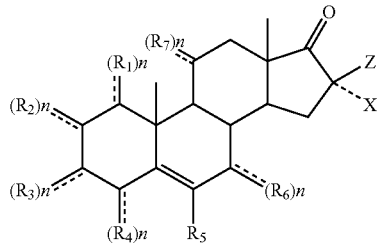

Formula I

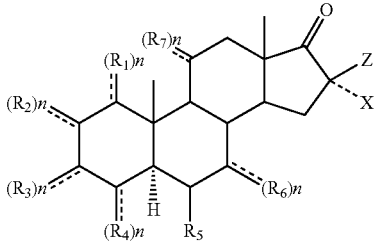

Formula II

39 Claims, No Drawings

TOPICAL STEROIDAL FORMULATIONS

RELATED APPLICATION

This application claims the benefit of U.S. Provisional Application No. 61/076,784, filed on Jun. 30, 2008. The entire teachings of the above application are incorporated herein by reference.

GOVERNMENT SUPPORT

The invention was supported, in whole or in part, by a grant CA-12227 from National Cancer Institute. The Government has certain rights in the invention.

BACKGROUND OF THE INVENTION

Some of the compounds of Formulae I and II are generally useful as anti-cancer, anti-obesity, anti-diabetic, anti-coronary agents, anti-aging agents, anti-hypolipidemic agents and anti-autoimmune agents. (Schwartz et. al., U.S. Pat. Nos. 5,656,621; 4,898,694; 5,001,119, 5,028,631; 5,157,031, 5,696,106; 5,700,793; 5,714,481, 5,804,576). In particular, 16α-fluoro-5-androsten-17-one (fluasterone) has been shown to have reduced androgenic effects while maintaining the therapeutic effects in comparison to dehydroepiandrosterone (DHEA). (McCormick et. al., Carcinogenesis 2007 28(2): 398-403). Fluasterone has been shown to improve recovery from traumatic brain injury in rat model of traumatic brain injury. (Malik et. al. Journal of Neurotrauma 20:463-476, 2003). Furthermore, Fluasterone is also known to inhibit collagen-induced arthritis in mice, indicating efficacy against rheumatoid arthritis. (Offfier et. al, Clinical Immunology, 110 (2), 2004, 181-190; Williams J. R. et. al., Methods in Molecular Medicine, 2004, 98, 207-216). Fluasterone treatment inhibits the acute inflammatory and hyperplastic effects of 12-O-tetradecanoylphorbol-13-acetate (TPA) induced skin papilloma formation. (Schwartz et. al. Cancer Res. 48:4817 4822, 1988; Schwartz et. al., Carcinogenesis 10:1809-1813, 1989; Pashko et. al. Carcinogenesis 12:2189-2192, 1991; Hastings et. al., Carcinogenesis 9:1099-102, 1988).

Problems associated with steroidal compositions include the androgenicity and poor oral availability associated with them. For example, clinical trials with DHEA are encumbered by the high oral doses required as well as the conversion of DHEA into active androgens. The use of less androgenic congeners as well as non-oral formulations may facilitate testing of this class of compounds. (Schwartz et. al., Ageing Research Reviews, 3(2), 2004, 171-187. The formulations herein address solubility problems associated with insoluble pharmaceutical agents, and allows the preparation of topical formulations of compositions with low androgenicity.

Compounds of Formula I and II are useful against a wide variety of diseases, including cancer, diabetes and metabolic syndrome. For example, fluasterone due to its reduced androgenic effect would be useful for chemoprevention.

Glucocorticoids are a widely used class of steroid hormones, but are associated with significant side effects. Glucocorticoids are characterized by an ability to bind with the glucocorticoid receptor. (Thomas et. al., U.S. Patent Publication No. 20060069071). Topical glucocorticoids are well known to cause local skin atrophy (thinning of the skin), purpura (bruised-appearing skin), striae ("stretch marks"), tolerance and "addiction syndrome". Combined dehydroepiandrosterone-glucocorticoid compositions have been described as effective pharmaceutical treatments for dermatitis. (Thomas et. al., WO2006/036484). Furthermore, DHEA is known to have antiglucocorticoid effects in the brain. (R. Morfin, DHEA and the brain, Wiley, 2002, 52-53). However, DHEA is known to have androgenic side effects. As such, it would be advantageous to have compositions with reduced androgenicity to reduce side effects associated with glucocorticoids.

Inhibition of G6PDH was believed to be a critical mechanism by which DHEA and DHEA analogs reduce inflammation and oxygen free radical formation. (Schwartz et. al., Ageing Res. Reviews. 3:171-187, 2004). The effectiveness of fluasterone against TPA-induced skin papilloma formation was believed to be mediated by the inhibition of glucose 6-phosphate dehydrogenase (G6PDH) with a consequent lowering of NADPH levels and reactive oxygen formation. (Schwartz et. al., Cancer Lett. 168:7-14, 2001). Without being bound by any mechanism, the data herein indicate that G6PDH inhibition may not be the mechanism by which these steroids produce an anti-glucocorticoid effect. Compound 8356 (16α-fluoro-5α-androstan-17-one) is a more potent G6PDH inhibitor than fluasterone yet it is about ⅛ as active in protecting against dexamethasone. (Schwartz et. al., Cancer Res., 48:4817 4822, 1988). However, due to poor water solubility oral bioavailability of fluasterone has required very high dosage levels. Nanosized fluasterone formulations were shown to have better bioavailability than unmilled and micronized formulations. (Janjikhel, et. al., AAPS Annual Meeting Abstracts, 2002). Even nanosized formulations required very high dosages (100 mg/kg) for oral delivery.

Thus, fluasterone is difficult to formulate, particularly for topical administration, due at least in part, to its very low water solubility. Therefore, a need exists to provide new formulations for the administration of fluasterone.

SUMMARY OF THE INVENTION

The present invention generally relates to formulations of poorly water soluble agents for pharmaceutical or veterinary use. The formulations of the present invention can be used for oral, topical, sublingual, buccal, intradermal, nebulization or inhalation methods of administration of poorly water soluble pharmaceutical agents. The present invention further relates to the delivery of poorly water soluble compounds of Formulae I and II.

Formula I:

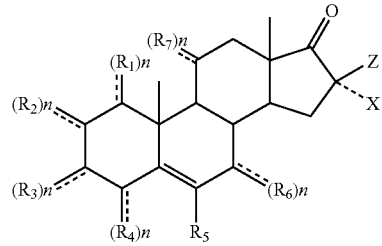

Formula II:

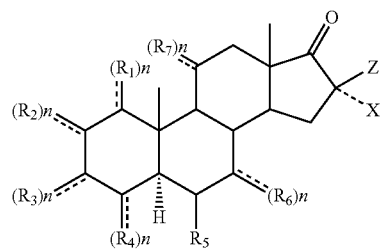

wherein $R_1$, $R_2$, $R_3$, $R_4$, $R_5$, $R_6$, and $R_7$ are each individually hydrogen or lower alkyl or hydroxyl or alkoxy having 1 to 5 carbons;

X is halogen, hydroxyl, hydrogen, lower alkyl or lower alkoxy having 1 to 5 carbons;

Z is hydrogen or lower alkyl or alkoxy having 1 to 5 carbons, and n is 1 or 2;

wherein at least one of X and Z is other than hydrogen.

The formulations of the present invention are particularly useful for topical use because they dry quickly while providing an emollient effect. One of the advantages of the co-solvent used herein is its water solubility, which enables one to readily wash it off one's skin. Furthermore, the formulations herein are useful for topical (including buccal and sublingual), vaginal and parenteral (including subcutaneous, intramuscular, intradermal, intrathecal and epidural) delivery of compounds with poor oral availability.

Another aspect of the present invention is the use of compounds of formula I and II to alleviate the side effects of corticosteroid treatments. This invention in particular relates to co-administration of fluasterone with glucocorticoids. Applicants have surprisingly found that fluasterone has high potency when compared to several other related steroids, including DHEA, in protecting mice against dexamethasone-induced thymic involution. This marked anti-glucocorticoid activity can be particularly useful to treat cancer patients.

Another aspect of the invention is the preparation of micronized and nano-sized particles of formulae I and II, particularly fluasterone. These smaller sized particles of compounds of formulae I and II can be particularly useful for topical applications. Such micronized and nano-sized particles of compounds of formulae I and II, particularly fluasterone, is useful for the treatment of diabetes, obesity and metabolic syndrome.

The compositions herein are useful for the treatment of diabetes, obesity related diseases and metabolic syndromes. The compositions herein are further useful for the treatment of arthritis, including rheumatoid arthritis and osteoarthritis, skin diseases including dermatitis, atherosclerosis and cancer. In addition to its chemopreventive activity, fluasterone protects against neoplastic development in a number of tissues including the prostate and other epithelial tissues. The compositions herein are particularly useful as anti-cancer, anti-proliferative agents against tumors and cancers relating to prostate, mammary gland, skin, colon, lung, lymphatic system, liver and rat thyroid.

Topical applications of the instant application are particularly useful for the treatment of osteoarthritis of the joints. In particular the hand, foot, thumb, forearm, knees, hip, jaw and elbow joints can be treated locally with topical applications containing compounds of formula I and II. Metacarpophalangeal, temporomandibular, trapeziometacarpal, metatarsal, carpus, ginglymus and sternoclavicular articulation joints can be treated with compositions of the instant application.

DETAILED DESCRIPTION OF THE INVENTION

A description of preferred embodiments of the invention follows.

This invention is based, at least in part, of the discovery that formulations of fluasterone, and related compounds, can be made by combining the compound with organic alcohols, such as ethanol, and polysorbates, such as a Tween compound (e.g. Tween 80) and solubilizing the compound. Additional components or excipients can be added to the resulting solution, such as a viscosity enhancing agent or a gelling agent. Formulations made according to the invention can be topically applied, achieving good to excellent absorption without creating an uncomfortable feeling on the skin.

In one aspect, the present invention relates to formulations containing compounds of Formula I and II.

Formula I:

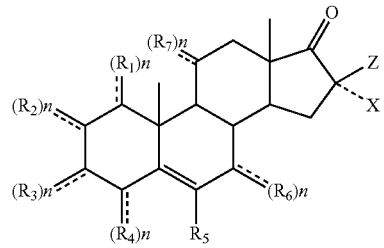

Formula II:

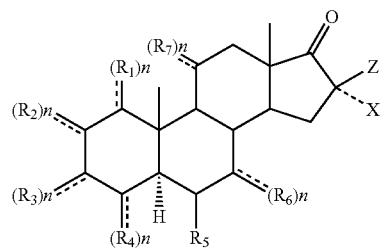

wherein $R_1$, $R_2$, $R_3$, $R_4$, $R_5$, $R_6$, and $R_7$ are each individually hydrogen or lower alkyl or hydroxyl or alkoxy having 1 to 5 carbons;

X is halogen, hydroxyl, hydrogen, lower alkyl or lower alkoxy having 1 to 5 carbons;

Z is hydrogen or lower alkyl or alkoxy having 1 to 5 carbons, and n is 1 or 2;

wherein at least one of X and Z is not hydrogen.

The stereochemistry of various substituents are designated as being in the α-position by means of a broken line (---) joining the substituent to the steroid nucleus. The substituents are designated as being in the β-position by means of a solid line (-) joining the substituent to the steroid nucleus. In those cases in which the substituents may be either in the α or β positions, the substituents are indicated as being joined to the steroid nucleus by a broken line and a solid line placed side to side. The compounds of formula I and II can be prepared by methods described in U.S. Pat. Nos. 5,656,621; 4,898,694; 5,001,119, 5,028,631; 5,157,031; 5,696,106; 5,700,793; 5,714,481, the entire contents of which are incorporated by reference herein.

The following compounds of formula I and II are preferred; 3β-methyl-16α-fluoro-5-androsten-17-one, 16α-methyl-5-androsten-17-one, 3β-methyl-5-androsten-17-one, 3β-methyl-16α-methyl-5-androsten-17-one, 3β-methyl-16α-chloro-5-androsten-17-one, 16α-fluoro-5α-androstan-17-one (8356), 7α-hydroxyfluasterone, 16α-fluoro-5-androsten-17β-ol, 16α-hydroxy-5-androsten-17-one and 16α-fluoro-5-androsten-17-one (fluasterone) is more preferred.

Compounds of formula I and II, including fluasterone suffer from poor solubility in water and require high oral doses in animals to produce efficacy. The lowest effective oral dose of fluasterone which abolishes 12-O-tetradecanoylphorbol-13-acetate (TPA)-stimulated epidermal hyperplasia in mouse skin was determined to be 200 mg/kg, whereas when administered by subcutaneous injection, the lowest effective dose was 2.5-5 mg/kg. The same dose relationship was observed in BKS. Cg-m$^+$/$_+$ Lepr$^{db}$ diabetic mice for efficacy in lowering fasting plasma glucose and triglyceride levels. Orally-administered $^{14}$C-Fluasterone undergoes extensive first-pass hepatic and/or gastrointestinal metabolism, thus necessitating high oral doses to achieve efficacy.

In dose-response experiments the anti-hyperplastic efficacy of fluasterone in TPA-treated mouse epidermis to determine bioavailability following different routes of administration was measured. Mice were treated with a single dose of fluasterone (either orally, subcutaneously, or transdermally) followed by a single application of TPA to the shaved back one hour latter. In case of transdermal administration, fluasterone is applied in a topical formulation to the shaved abdomen to allow for systemic absorption to the back of the animal. Twenty hours after TPA application, the mice are injected with 60 µCi of [3H] thymidine, sacrificed 20 minutes later, and a 2×2 cm2 of skin from the shaved back is excised and processed for the determination of the amount of [3H] thymidine incorporated per unit of epidermal DNA. (Hennings et. al., *Cancer Res.* 28:543-552, 1968).

Topical application of TPA produces a 2-to-4-fold increase in both the cpm of [$^3$H] thymidine per µg epidermal DNA as well as a 2-to-4-fold increase in the epidermal DNA content per 2×2 cm2 of skin. This hyperplastic effect of TPA, as well as its reversal by fluasterone, has been confirmed by histological examination of the mouse skin (Schwartz and Pashko, Cancer Lett. 168:7-14, 2001).

The lowest dose of orally-administered fluasterone which abolishes TPA-stimulated epidermal [$^3$H] thymidine incorporation and epidermal DNA content is 200 mg/kg. This is also the lowest reported oral dose which inhibits TPA-promoted skin tumor promotion (Schwartz, et al. *Carcinogenesis* 10:1809-1813, 1989)). This is also the lowest oral dose which lowers fasting plasma glucose in diabetic mice. In the TPA test as the oral dose is increased beyond 200 mg/kg, there is an increase in the rate of [$^3$H] thymidine incorporation per unit of DNA, whereas the epidermal DNA content per 2×2 cm$^2$ of skin remains depressed. This "U-shaped" dose-response is seen with all routes of administration and presumably results from a decrease in the endogenous thymidine pool size as a consequence of G6PDH inhibition (Nyce, J. W. *Cellular and molecular aspects of 1,2-dimethylhydrazine-induced murine colonic adenocarcinomas, and their inhibition by dehydroepiandrosterone*. Ph.D Thesis, Temple University, pp 35-37, University Microfilms Int., Ann Arbor, Mich., 1983).

Transdermal administration of fluasterone was as potent as subcutaneous injection in abolishing TPA-stimulated hyperplasia.

Compositions according to the invention are especially advantageous for the topical administration to the skin of human subjects of fluasterone and similar water insoluble steroidal drugs. One or more compounds of the invention (herein referred to as the active ingredients) are administered by any route appropriate to the condition to be treated. Suitable topical routes include oral, rectal, nasal, topical (including buccal and sublingual), and vaginal, preferably across the epidermis. Although not preferred, the compositions of the invention can also be used for parenteral administration (including subcutaneous, intramuscular, intradermal, intrathecal and epidural), and the like. It will be appreciated that the preferred route may vary with for example the condition of the recipient. An advantage of the compositions of this invention is that they can be topically administered.

Some of the examples of methods for formulating transdermal compositions that may be useful for formulating compositions herein are disclosed in U.S. Pat. Nos. 7,198,801 and 7,244,703. Cyclopentadecalactone and cyclohexadecanone may be useful as additives in formulating transdermal compositions herein.

Pretreatment of C3H/HeN mice with s.c. DHEA (60 mg/kg) for 3 days significantly reduces dexamethasone (DEX)-induced thymic and splenic atrophy one day after a single DEX dose (1.6 mg) (Blauer et. al., *Endocrinology* 129:3174-3179, 1991). Using this model, we confirmed that DHEA at a dose of 60 mg/kg significantly protected CD-1 mice against DEX-induced thymic and splenic atrophy, but was inactive at a dose of 10 mg/kg or 20 mg/kg. In contrast, fluasterone at a dose of 10 mg/kg was as active as DHEA at 60 mg/kg and also showed significant protection at a dose of 5 mg/kg.

In addition to fluasterone and DHEA, nine other related steroids were tested for efficacy in protecting mice against DEX-induced thymic and splenic involution. Fluasterone was the most active steroid tested, with the steroid 3β-methyl-5-androsten-17-one showing almost as great potency. The other steroids tested were all significantly less active than fluasterone. The various steroids tested, as well as their potency as compared to fluasterone, are shown in the following table.

TABLE 1

Relative potency against Dexamethasone induced thymic and splenic atrophy.

| Steroid | Approximate Potency Compared to Fluasterone in Protecting Against DEX-induced Thymic and Splenic Involution |
|---|---|
| Fluasterone | 1 |
| DHEA | about ⅙ |
| 16α-fluoro-5α-androstan-17-one (8356) | about ⅛ |
| 7α-hydroxyfluasterone | about ½ |
| 16α-methyl-5-androsten-17-one | about ⅙ or less |
| 16α-hydroxy-5-androsten-17-one | about ¹⁄₁₂ |
| 16α-fluoro-5-androsten-17β-ol | <¹⁄₁₂ |
| 3β-methyl-5-androsten-17-one | slightly less active |
| 3β-methyl-16α-fluoro-5-androsten-17-one | <½ |
| 3β-methyl-16α-chloro-5-androsten-17-one | about ⅙ or considerably less |
| 3β-methyl-16α-methyl-5-androsten-17-one | about ⅙ |

The compositions of the present invention are also useful for the treatment or prevention of diabetes as well as treatment and prevention of obesity. Without being bound by any theory, the observations herein indicate that the anti-glucocorticoid action of these steroids may be responsible for their anti-obesity activity. Very likely, the anti-glucocorticoid action is the primary mechanism of the anti-diabetic effect as well.

The compositions of the present invention are useful for the treatment, control, or prevention of obesity-related disorders. The obesity-related disorders herein are associated with, caused by, or result from obesity. Examples of obesity-related disorders include diabetes, overeating, binge eating, and bulimia, hypertension, elevated plasma insulin concentrations and insulin resistance, dyslipidemias, hyperlipidemia, endometrial, breast, prostate, kidney and colon cancer, osteoarthritis, obstructive sleep apnea, gallstones, heart disease, abnormal heart rhythms and arrythmias, myocardial infarction, congestive heart failure, coronary heart disease, sudden death, stroke, polycystic ovary disease, craniopharyngioma, atherosclerosis, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastro-esophageal reflux, breathlessness, respiratory disorders, such as obesity-hypoventilation syndrome (Pickwickian syndrome), cardiovascular disorders, inflammation, such as systemic inflammation of the vasculature, atheriosclerosis, hypercholesterolemia, hyperuricaemia, lower back pain, gallbladder disease, hyperuricemia, gout, and kidney cancer, and increased anesthetic risk. The compositions of the present invention are also useful to treat Alzheimer's disease.

Dyslipidemias or disorders of lipid metabolism, include various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., Journal of the American Medical Association, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-m. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

The term "obesity" as used herein is a condition in which there is an excess of body fat. The operational definition of obesity is based on the Body Mass Index (BMI), which is calculated as body weight per height in meters squared (kg/m$^2$). "Obesity" refers to a condition whereby an otherwise healthy subject has a Body Mass Index (BMI) greater than or equal to 30 kg/m$^2$ or a condition whereby a subject with at least one co-morbidity has a BMI greater than or equal to 27 kg/m.sup.2. An "obese subject" is an otherwise healthy subject with a Body Mass Index (BMI) greater than or equal to 30 kg/m$^2$ or a subject with at least one co-morbidity with a BMI greater than or equal to 27 kg/m$^2$. A "subject at risk of obesity" is an otherwise healthy subject with a BMI of 25 kg/m$^2$ to less than 30 kg/m$^2$ or a subject with at least one co-morbidity with a BMI of 25 kg/m$^2$ to less than 27 kg/m$^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 kg/m$^2$. In Asian countries, including Japan, an "obese subject" refers to a subject with at least one obesity-induced or obesity-related co-morbidity that requires weight reduction or that would be improved by weight reduction, with a BMI greater than or equal to 25 kg/m$^2$. In Asia-Pacific, a "subject at risk of obesity" is a subject with a BMI of greater than 23 kg/m$^2$ to less than 25 kg/m$^2$.

Obesity-induced or obesity-related co-morbidities include, but are not limited to, diabetes, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type 2 diabetes, polycystic ovary disease, cardiovascular diseases, osteoarthritis, dermatological disorders, hypertension, insulin resistance, hypercholesterolemia, and hypertriglyceridemia.

Topical applications of the instant application are also useful for the treatment of osteoarthritis of the joints. In particular the hand, foot, thumb, forearm, knees, hip, jaw and elbow joints can be treated locally with topical applications containing compounds of formula I and II. Metacarpophalangeal, temporomandibular, trapeziometacarpal, metatarsal, carpus, ginglymus and sternoclavicular articulation joints can be treated with compositions of the instant application.
Formulations of Poorly Water Soluble Compounds:

The applicants have surprisingly found that certain mixtures of surfactants and/or organic alcohols can significantly improve the solubility of compounds of formula I. Such improved solubility is useful for preparing pharmaceutical formulations containing compounds of formula I and TI for topical, oral and subcutaneous administration. Preferable surfactants include polysorbates, and long-chain organic alcohols, including cetyl alcohol, stearyl alcohol etc. Polysorbate is used as the preferred surfactant, with Polysorbate 80 (polyoxyethylene (20) sorbitan monooleate; Tween 80) being an especially preferred surfactant. Sorbitan monooleate or other polysorbates with varying polyoxyethylene chain lengths can also be used. Straight chain organic alcohols with chain lengths in the range of 8-30 carbons are also useful as surfactants. Especially preferred carbon chain length is in the range of 14-24. Such compounds can correspond to the formula $CH_3(CH_2)_n$—OH, wherein n is 13-23. Another group of compounds useful as surfactants is polyethyleneglycol conjugated fatty acids and alcohols. Particularly preferred in this group of surfactants are the polyethyleneglycol stearate (MYRJ™ 45), Macrogol stearyl ether 2 (BRIJ™ 72), Macrogol stearyl ether 20 (BRIJ™ 72P), Macrogol stearyl ether 20-23 (BRIJ™ 35P), Macrogol stearate 40-50 (MYRJ™ 52S), Macrogol stearate 100 (MYRJ™ 25P), Macrogolglycerol hydroxystearate 25 (ATLAS™), Macrogolglycerol lauryl ether 9 and Macrogolglycerol lauryl ether 9. Sorbitan substituted fatty acids are also useful as surfactants in formulations of Formula I and II. For example, Sorbitan laureate, Sorbitan stearate, Sorbitan oleate and Sorbitan trioleate can be used.

In one embodiment, the formulations herein can be in the form of aqueous gel, anhydrous gel, a water-in-oil emulsion, oil-in-water emulsion or a suspension. Examples of gel forming procedure for DHEA can be found in U.S. Pat. Nos. 5,709,878, and 4,978,532 the entire content of which are incorporated by reference herein. Gels are semisolid systems of either containing suspended small inorganic particles (two phase gels) or organic macromolecules interpenetrated by a liquid (single phase gels). Emollients such as petrolatum, paraffin wax, beeswax, cetyl palmitate, and lanolin can be included in the formulations herein. When formulated for presentation as a gel, the composition of the invention can include a gelling agent such as a finely divided solid and/or a thickener in concentrations that produce a loose molecular network inhibiting the free movement of liquid ingredients. Thus a typical gel composition of the invention includes a concentration of a compound of Formula I or II in the range of about 0.1 to about 20 grams per 100 grams of composition, preferably about 0.25 to about 5 grams per 100 grams; a concentration of phospholipid in the range of about 2 to about 50 grams per 100 grams of composition, preferably about 3 to about 25 grams per 100 milliliters; a concentration of finely divided solid in the range of about 0 to about 15 grams per 100 grams of composition, and a concentration of thickener in the range of about 0 to about 15 grams per 100 grams of composition.

Gellants may also be included in the formulations. These agents are typically non-ionic or cationic polymers such as hydroxyethyl cellulose, methylcellulose, guar gum, xanthan gum, hydroxypropylcellulose and cationic cellulosics. A particular example is Sepigel.

In one embodiment, a gel comprising a compound of formula I or II, can be made by mixing a lower alkyl alcohol, a polysorbate, water and a compound of formula I or II and, optionally, adding and mixing a thickening agent followed by incubating the ingredients until gel formation. Various temperatures may be used for incubation to effect gel formation. A preferred temperature range is about 3° C. to about 90° C.; a more preferred range is about 10° C. to about 50° C.; and more preferred range is about 10° C. to about 40° C. Incubation times vary depending on the temperature, and the ratio of ingredients. The ratios of ingredients may also vary depending on the particular compound of formula I or II and the particular lower alcohol use. The composition may comprise alcohol in the range of from about 20 to about 95% (v/v); preferably from about 30 to about 90%; even more preferably about 50 to about 90%. The water content may from about 0 to about 60%; preferably about 2 to about 40%; more preferably about 5 to about 30%; even more preferably about 15 to about 30%. The surfactant may be present in the range of about 0 to 10%; more preferably about 0.01% to about 5%; even more preferably about 0.01% to about 3.5%.

Examples of thickening agents that can be added to the gel or solution formulations described herein include: cellulosic thickening agents, for example, cellulose, hydroxyethyl-cellulose, carboxymethylcellulose, and hydroxypropylmethylcellulose; and acrylic thickening agents. Examples of preferred acrylic thickeners are carbomers, for example, nonlinear polymers of acrylic acid cross-linked with a polyalkenyl polyether. Examples of preferred carbomers which may be used in the present invention include carboxypolymethylene, carboxyvinyl polymer, and alkyl acrylates, for example, acrylic acid/alkyl methacrylate copolymer. All of the above are available from Noveon, with carboxypolymethylene sold as Carbopol 980®, carboxyvinyl polymer sold as Carbopol 940®, and acrylic acid/alkyl methacrylate copolymer sold as Pemulen TR-1®.

In a preferred embodiment, the formulations of the invention can be applied by misting or spraying the formulation on the skin either via a metered dose device or from a unit dose container. In this method, the formulation can be distributed evenly over a larger area thereby providing a quick means for absorption. Alternatively the formulation can be applied via an applicator, such as a roll-on applicator, a metered pump dispenser or sponge.

In one embodiment, the composition of this invention is administered to the recipient by means of a transdermal delivery system or patch. Transdermal delivery is accomplished by exposing a source of the substance to be administered to the recipient's skin for an extended period of time. Typically, the formulation is incorporated in or absorbed on a matrix or container from which it is released onto the recipient's skin. The rate of release can be controlled by a membrane placed between the container and the skin, by diffusion directly from the container, or by the skin itself serving as a rate-controlling barrier. Many suitable transdermal delivery systems and containers therefore are known, ranging in complexity from a simple gauze pad impregnated with the substance to be administered and secured to the skin with an adhesive bandage to multilayer and multi-component structures. Some of the systems are characterized by the use with the substance to be administered of a shaped article sufficiently flexible to snugly fit to the skin of the recipient and thus serve both as container from which the substance is delivered to the recipient's skin and as barrier to prevent loss or leakage of the substance away from the area of the skin to which the substance is to be delivered. A transdermal delivery system or patch may also contain an added substance that assists the penetration of the active ingredient through the skin, usually termed a skin enhancer or penetration enhancer. Transdermal delivery systems may contain an ethoxylated oil such as ethoxylated castor oil, ethoxylated jojoba oil, ethoxylated corn oil, and ethoxylated emu oil. An alcohol mixed with the ethoxylated oil may form a penetration enhancer.

A topical oil-in-water emulsion composition can be prepared by making a solution of fluasterone (or related compound) as described above and adding an immiscible phase (e.g., a biocompatible oil phase) and an optional emulsifying agent. An irritation mitigating agent can also be included, such as $C_{12-15}$ alkyl benzoate, octyl methoxycinnamate, octyl dimethyl PABA, octocrylene, menthyl anthranilate, and homomenthyl salicylate.

In certain preferred embodiments a foam comprising compounds of instant application can be prepared. An example of a foam forming procedure can be found in U.S. Pat. No. 7,141,237. For instance, an active agent in a solution as described herein and a quick-breaking foaming agent comprising a mixture of cetyl alcohol and stearyl alcohol, which are dissolved in the ethanol solution can be used. Preferably, this composition is packaged in a polyamide-imide-lined aluminum can and pressurized with a propane/butane mixture as the propellant. Under the packaged pressure, the hydrocarbon propellant liquefies and becomes miscible with the water/ethanol solution.

The formulation herein may contain an emulsifier and/or surfactant. A wide variety of such agents can be employed. In one embodiment, the compositions of the present invention comprise from about 0.05% to about 95%, preferably from about 10% to about 80%, and more preferably from about 3.5% to about 60% of at least one surfactant. The surfactant, at a minimum, must be hydrophilic enough to disperse in ethanol or other solvent system. The surfactants useful herein can include any of a wide variety of cationic, anionic, zwitterionic, and amphoteric surfactants disclosed in prior patents and other references. The exact surfactant chosen will depend upon the pH of the composition and the other components present.

In one embodiment, the composition comprises a hydrophilic emulsifier or surfactant. The compositions of the present invention preferably comprise from about 0.05% to about 5%, more preferably from about 0.05% to about 3.5% of at least one hydrophilic surfactant. Without intending to be limited by theory, it is believed that the hydrophilic surfactant assists in dispersing hydrophobic materials.

Preferred hydrophilic surfactants are selected from nonionic surfactants. Among the nonionic surfactants that are useful herein are those that can be broadly defined as condensation products of long chain alcohols, e.g. C8-30 alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a C8-30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8-20 alkyl group, and n is an integer of from about 1 to about 9. Commercially available examples of these surfactants include decyl polyglucoside and lauryl polyglucoside.

Other useful nonionic surfactants include the condensation products of alkylene oxides with fatty acids (i.e. alkylene oxide esters of fatty acids); the condensation products of alkylene oxides with 2 moles of fatty acids (i.e. alkylene oxide diesters of fatty acids); the condensation products of alkylene oxides with fatty alcohols (i.e. alkylene oxide ethers of fatty alcohols); and the condensation products of alkylene oxides with both fatty acids and fatty alcohols. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Other nonionic surfactants suitable for use herein include sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, and mixtures thereof. Nonlimiting examples of these non-silicon-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof. Commercially available surfactants include polysorbate 80 (Tween 80), polysorbate 20 (Tween 20), polysorbate 40 (Tween 40) and polysorbate (60). The preferred surfactants include polysorbates and more preferred surfactant is Tween 80.

Other emulsifiers useful herein are fatty acid ester blends based on a mixture of sorbitan or sorbitol fatty acid ester and sucrose fatty acid ester, the fatty acid in each instance being preferably C8-C24, more preferably C10-C20. The preferred fatty acid ester emulsifier is a blend of sorbitan or sorbitol C16-C20 fatty acid ester with sucrose C10-C16 fatty acid ester, especially sorbitan stearate and sucrose cocoate.

The hydrophilic surfactants useful herein can alternatively or additionally include any of a wide variety of cationic, anionic, zwitterionic, and amphoteric surfactants known in the art. The cationic surfactants useful herein include cationic ammonium salts such as quaternary ammonium salts, and amino-amides.

A wide variety of anionic surfactants are also useful herein. Nonlimiting examples of anionic surfactants include the alkoyl isethionates (e.g., C12-C30), alkyl and alkyl ether sulfates and salts thereof, alkyl and alkyl ether phosphates and salts thereof, alkyl methyl taurates (e.g., C12-C30), and soaps (e.g., alkali metal salts, e.g., sodium or potassium salts) of fatty acids.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably C8-C 18) and one contains an anionic water solubilizing group, e.g., carboxy, sulfonate, sulfate, phosphate, or phosphonate. Examples are alkyl imino acetates, and iminodialkanoates and aminoalkanoates, imidazolinium and ammonium derivatives. Other suitable amphoteric and zwitterionic surfactants are those selected from the group consisting of betaines, sultaines, hydroxysultaines, alkyl sarcosinates (e.g., C12-C30), and alkanoyl sarcosinates.

The compositions hereof, and especially the emulsions hereof, may contain a structuring agent. Structuring agents are particularly preferred in the oil-in-water emulsions of the present invention. Without being limited by theory, it is believed that the structuring agent assists in providing rheological characteristics to the composition which contribute to the stability of the composition. For example, the structuring agent tends to assist in the formation of the liquid crystalline gel network structures. The structuring agent may also function as an emulsifier or surfactant. Preferred compositions of this invention comprise from about 1% to about 90%, more preferably from about 1% to about 60% of one or more structuring agents.

Suitable structuring agents of the present invention are selected from the group consisting of palmitic acid, stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from the group consisting of stearic acid, palmitic acid, stearyl alcohol, cetyl alcohol, behenyl alcohol, steareth-2, and mixtures thereof.

Another aspect of the invention herein is the use of nanosized compounds of formula I and II, in particular fluasterone, for topical administration. Because of the high adhesiveness of nanoparticles on biological surfaces (e.g., epithelial gut wall), nanoparticulate technology may prolong the absorption time of poorly soluble drugs, thereby improving bioavailability. There are several well known methods for the preparation of nanosized pharmaceuticals. For example, wet milling or piston gap homogenization can be used to nanosize fluasterone. For discussions related to wet milling, see, e.g., U.S. Pat. No. 5,518,187 to J. A. Bruno et al.; U.S. Pat. No. 5,862,999 (D. A. Czekai and L. P. Seaman); and U.S. Pat. No. 5,534,270 (L. De Castro); for discussions related to piston gap homogenization, see U.S. Pat. No. 5,543,133 (J. R. Swanson et al.); U.S. Pat. No. 5,858,410 (R. H. Muller et al.); U.S. Patent Publication No. 2003/0072807 A1 (J. C-T. Wong et al.); and U.S. Pat. No. 5,510,118 (H. W. Bosch et al.), the complete disclosures of which are herein incorporated by reference. Wet milling is a well understood process, which relies on impact and shear forces to reduce particle size. Piston gap homogenization, which utilizes cavitation forces and impact or shear forces to reduce particle size. A method involving high-pressure spray homogenizer can also be used to prepare nanosized particles. (Galli et. al. U.S. Patent Publication No. 20070020197).

The nanosized or micronized compounds of formula I and II can be part of a delivery matrix. For example, matrix carrier can be an amorphous microporous non-fibrous silicon or titanium oxide similar to those described in U.S. Patent Publication No. 20070275068 can be used. Sol-gel processed drug-silica composite materials have been investigated for controlled drug release. One concept involving the use of sol-gel type silica is the synthesis of a bio-erodible silica-drug composite. Silica-based drug release systems prepared using sol-gel approaches in which compounds of formulae I and II are introduced during polymerisation and processing of the silica matrix can be used for drug delivery. An alternative approach for making a drug delivery system based on silica gels is the synthesis of silica in the absence of compounds of formulae I and II, followed by drying and calcination to obtain a xerogel and then by loading the calcinated material with the appropriate compound. The sol-gel approach enables the synthesis of a large variety of silica materials. Micropores with very narrow pore size distribution can be obtained through calcinations which can be useful for the delivery of micronized or nano-sized compounds of formulae I and II, particularly for topical delivery.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese.

The compositions of the present invention are useful for treating both Type 1 and Type 2 diabetes. The term "diabetes associated with obesity" refers to diabetes caused by obesity or resulting from obesity. The compositions are especially effective for treating Type 2 diabetes. The compositions of the present invention are also useful for treating and/or preventing gestational diabetes mellitus.

Diabetes is characterized by a fasting plasma glucose level of greater than or equal to about 126 mg/dl. A diabetic subject has a fasting plasma glucose level of greater than or equal to about 126 mg/dl. Prediabetes is characterized by an impaired fasting plasma glucose (FPG) level of greater than or equal to about 110 mg/dl and less than about 126 mg/dl; or impaired glucose tolerance; or insulin resistance. A prediabetic subject is a subject with impaired fasting glucose (a fasting plasma glucose (FPG) level of greater than or equal to about 110 mg/dl and less than about 126 mg/dl); or impaired glucose tolerance; or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensitivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The terms "administration of" and or "administering a" compound should be understood to mean providing a compound of the invention or a prodrug of a compound of the invention to a subject in need of treatment. The instant pharmaceutical compositions include administration of a single pharmaceutical dosage formulation which contains the anti-obesity agent and an anti-hypertensive agent, for example, as well as administration of each active agent in its own separate pharmaceutical dosage formulation. Where separate dosage formulations are used, the individual components of the composition can be administered at essentially the same time, i.e., concurrently, or at separately staggered times, i.e. sequentially prior to or subsequent to the administration of the other component of the composition. The instant pharmaceutical composition is therefore to be understood to include all such regimes of simultaneous or alternating treatment, and the terms "administration" and "administering" are to be interpreted accordingly. Administration in these various ways are suitable for the present compositions as long as the beneficial pharmaceutical effect of the combination of the anti-obesity agent and the anti-hypertensive agent is realized by the patient at substantially the same time. Such beneficial effect is preferably achieved when the target blood level concentrations of each active drug are maintained at substantially the same time. A single dosage formulation will provide convenience for the patient, which is an important consideration especially for patients with diabetes, metabolic syndrome, or obese patients who may be in need of multiple medications.

The term "subject", as used herein refers to an animal, preferably a mammal, most preferably a human, who has been the object of treatment, observation or experiment. In one embodiment the term "mammal" is a "human" said human being either male or female. The instant combinations are also useful for treating or preventing obesity and obesity-related disorders in cats and dogs. As such, the term "mammal" includes companion animals such as cats and dogs.

The term "subject in need thereof" refers to a subject who is in need of treatment or prophylaxis as determined by a researcher, veterinarian, medical doctor or other clinician. In one embodiment a subject in need thereof is a mammal. In another embodiment, a subject in need thereof is an obese and/or diabetic subject or a subject who is at risk of becoming diabetic.

The administration of the composition of the present invention in order to practice the present methods of therapy is carried out by administering a therapeutically effective amount of the compounds in the composition to a subject in need of such treatment or prophylaxis. The need for a prophylactic administration according to the methods of the present invention is determined via the use of well known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgment.

The term "therapeutically effective amount" as used herein means the amount of the active compounds in the composition that will elicit the biological or medical response in a tissue, system, subject, or human that is being sought by the researcher, veterinarian, medical doctor or other clinician, which includes alleviation of the symptoms of the disorder being treated. The novel methods of treatment of this invention are for disorders known to those skilled in the art.

The term "prophylactically effective amount" as used herein means the amount of the active compounds in the composition that will elicit the biological or medical response in a tissue, system, subject, or human that is being sought by the researcher, veterinarian, medical doctor or other clinician, to prevent the onset of diabetes, for example.

The magnitude of prophylactic or therapeutic dose of the active ingredients of the composition will, of course, vary with the nature of the severity of the condition to be treated and with the particular compound in the composition and its route of administration. It will also vary according to the age, weight and response of the individual patient In general, for treating, controlling, and/or preventing metabolic syndrome, the anti-hypertensive agent, the anti-obesity agent, the anti-diabetic agent and the anti-dyslipidemic agent in the combination are administered at a daily dosage of from about 0.0001 mg/kg to about 1000 mg/kg of body weight, preferably from about 0.001 mg/kg to about 100 mg/kg, given in a single dose or in divided doses two to six times per day, or in sustained release form. The dosage regimen may be adjusted to provide the optimal therapeutic response.

The compounds of this invention can be administered to humans in the dosage ranges specific for each compound. The effective dosage of each of the active ingredients employed in the composition may vary depending on the particular compound employed, the mode of administration, the condition being treated and the severity of the condition being treated.

Thus, the dosage regimen utilizing the compositions of the present invention is selected in accordance with a variety of factors including type, species, age, general health, body weight, diet, sex and medical condition of the subject; the severity of the condition to be treated; the renal and hepatic function of the patient; the drug combination; and the particular compounds employed and their routes of administration. A physician, clinician or veterinarian of ordinary skill can readily determine and prescribe the effective amount of the drug required to prevent, counter or arrest the progress of the condition.

Unless defined otherwise, all technical and scientific terms used herein have the same meaning as is commonly understood by one of skill in the art to which the claimed subject matter belongs. All patents, patent applications, published applications and publications, websites and other published materials referred to throughout the entire disclosure herein, unless noted otherwise, are incorporated by reference in their entirety. In the event that there are a plurality of definitions for terms herein, those in this section prevail. Reference thereto evidences the availability and public dissemination of such information. It is to be understood that both the foregoing general description and the following detailed description are exemplary and explanatory only and are not restrictive of the products, methods and other subject matter provided herein. In this application, the use of the singular includes the plural unless specifically stated otherwise. In this application, the use of "or" means "and/or" unless stated otherwise. Furthermore, use of the term "including" as well as other forms, such as "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Unless specific definitions are provided, the nomenclatures utilized in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients.

As used herein, the term "alkyl" refers to an aliphatic hydrocarbon group. An alkyl group can be a "saturated alkyl," which means that it does not contain any alkene or alkyne groups. An alkyl group can be an "unsaturated alkyl," which means that it contains at least one alkene or alkyne group. An alkyl, whether saturated or unsaturated, can be branched, straight chain, or cyclic.

As used herein, the term "lower alkyl" refers to an alkyl containing 1 to 5 carbon atoms. The term "medium alkyl" refers to an alkyl containing 5 to 10 carbon atoms. An alkyl can be designated as "$C_1$-$C_4$ alkyl" or similar designations. By way of example only, "$C_1$-$C_4$ alkyl" indicates an alkyl having one, two, three, or four carbon atoms, i.e., the alkyl is selected from among methyl, ethyl, propyl, iso-propyl, n-butyl, iso-butyl, sec-butyl, and t-butyl. Thus $C_1$-$C_4$ includes $C_1$-$C_2$ and $C_2$-$C_3$ alkyl. Alkyls can be substituted or unsubstituted. Alkyls include, but are not limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like, each of which can be optionally substituted.

Unless otherwise indicated, the term "optionally substituted," refers to a group in which none, one, or more than one of the hydrogen atoms has been replaced with one or more group(s) individually and independently selected from: cycloalkyl, aryl, heteroaryl, non-aromatic heterocycle, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono and di substituted amino groups, and the protected derivatives of amino groups. Such protective derivatives (and protecting groups that can form such protective derivatives) are known to those of skill in the art and can be found in references such as Greene and Wuts, above. In embodiments in which two or more hydrogen atoms have been substituted, the substituent groups can together form a ring.

As used herein, the term "pharmaceutical agent" refers to a chemical compound or composition capable of inducing a desired therapeutic effect in a patient. In certain embodiments, a pharmaceutical agent contains an active agent, which is the agent that induces the desired therapeutic effect. In certain embodiments, a pharmaceutical agent is a prodrug. In certain embodiments, a pharmaceutical agent contains inactive ingredients such as carriers, excipients, and the like.

As used herein, the term "therapeutically effective amount" refers to an amount of a pharmaceutical agent sufficient to achieve a desired therapeutic effect.

As used herein, the term "pharmaceutically acceptable" refers to a formulation of a compound that does not significantly abrogate the biological activity, a pharmacological activity and/or other properties of the compound when the formulated compound is administered to a patient. In certain embodiments, a pharmaceutically acceptable formulation does not cause significant irritation to a patient.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives can be readily prepared by those of skill in this art using known methods for such derivatization. The compounds produced can be administered to animals or humans without substantial toxic effects and either are pharmaceutically active or are prodrugs. The term "pharmaceutically acceptable salts" refers to the pharmaceutically acceptable and common salts, for example, a base addition salt to carboxyl group when the compound has a carboxyl group, or an acid addition salt to amino or basic heterocyclyl when the compound has an amino or basic heterocyclyl group, including quaternary ammonium salts, prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, trifluoro acetate, isothionate, triethiodide, lactate, panoate, valerate, and the like which can be used as a dosage form for modifying the solubility or hydrolysis characteristics or can be used in sustained release or prodrug formulations. The pharmaceutically acceptable salts of the composition of the instant invention include the composition wherein one of the individual components of the composition is in the form of a pharmaceutically acceptable salt, or the composition wherein all of the individual components are in the form of pharmaceutically acceptable salts (wherein the salts for each of the components can be the same or different), or a pharmaceutically acceptable salt of the combined components (i.e., a salt of the composition).

The "pharmaceutically acceptable esters" in the present invention refer to non-toxic esters, for example, the pharmaceutically acceptable, common esters on carboxyl group when the compound has a carboxyl group, for example, esters with lower alkyls (for example methyl, ethyl, propyl, isopropyl, butyl, sec-butyl, tert-butyl, pentyl, isopentyl, neopentyl, cyclopropyl, cyclobutyl, cyclopentyl), aralkyls (for example benzyl, phenethyl), lower alkenyls (for example allyl, 2-butenyl), lower alkoxy (lower) alkyls (for example methoxymethyl, 2-methoxyethyl, 2-ethoxyethyl), lower alkanoyloxy (lower) alkyls (for example acetoxymethyl, pivaloyloxy-methyl, 1-pivaloyloxyethyl), lower alkoxycarbonyl (lower) alkyls (for example methoxycarbonylmethyl, isopropoxycarbonylmethyl), carboxy-lower)alkyls (for example carboxymethyl), lower alkoxycarbonyloxy-(lower)alkyls (for example 1-(ethoxycarbonyloxy)ethyl, 1-(cyclohexyl-oxycarbonyloxy)ethyl), carbamoyloxy(lower)alkyls (for example carbamoyloxymethyl), phthalidyl group, (5-substituted-2-oxo-1,3-dioxol-4-yl)methyl (for example (5-methyl-2-oxo-1,3-dioxol-4-yl)methyl), and the like.

The nanosized particles employed in the composition has a median particle size of about 1 nm to about 2700 nm, preferably about 200 nm to about 2200 nm and more preferably about 300 nm to about 2200 nm, and even more preferably about 300 to about 2100 nm, most preferably about 300 nm to about 1000 nm.

As used herein, micronized refers to objects having an average size ranging from 1 μm to 1000 μm, as measured by light-scattering methods, microscopy, or other appropriate methods. The micronized compositions preferably have particle size in the range of about 1 μm to 1000 μm, more preferably about 1 μm to 100 μm, even more preferably about 1 μm to 50 μm, even more preferably about 1 μm to 25 μm, most preferably about 1 μm to 10 μm.

The compounds in the compositions of the present invention include stereoisomers, such as optical isomers, diastereomers and geometrical isomers, or tautomers depending on the mode of substitution. The compounds may contain one or more chiral centers and occur as racemates, racemic mixtures and as individual diastereomers, enantiomeric mixtures or single enantiomers, or tautomers, with all isomeric forms being included in the present invention. The present invention is meant to comprehend all such isomeric forms of the compounds in the compositions of the present invention, and their mixtures. Therefore, where a compound is chiral, the separate enantiomers, substantially free of the other, are included within the scope of the invention; further included are all mixtures of the two enantiomers. Also included within the scope of the invention are polymorphs, hydrates and solvates of the compounds of the instant invention.

As used herein, a "prodrug" refers to a pharmaceutical agent that is converted from a less active form into a corresponding more active form in vivo. A prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York).

As used herein, the term "co-administer" refers to administering more than one pharmaceutical agent to a patient. In certain embodiments, co-administered pharmaceutical agents are administered together in a single dosage unit. In certain embodiments, co-administered pharmaceutical agents are administered separately. In certain embodiments, co-administered pharmaceutical agents are administered at the same time. In certain embodiments, co-administered pharmaceutical agents are administered at different times.

As used herein "subject" is an animal, typically a mammal, including human.

As used herein, the term "patient" includes human and animal subjects.

Certain compounds that bind to glucocorticoid receptor and/or modulate an activity of such receptors play a role in health (e.g., normal growth, development, and/or absence of disease). In certain embodiments, selective glucocorticoid receptor modulators and/or binding compounds are useful for treating any of a variety of diseases or conditions. Certain compounds have been previously described as receptor modulators. See e.g., U.S. Pat. Nos. 5,693,646; 6,380,207; 6,506,766; 5,688,810; 5,696,133; U.S. Patent Publication No. 20070281959; Zhi, et. al. Bioorganic & Medicinal Chemistry Letters 2000, 10, 415-418; Pooley, et. al., J. Med. Chem. 1998, 41, 3461, the entire disclosures of which are incorporated herein in their entirety.

Estimation of Human Transdermal Dose

The following approach to estimate human dose.

1. Comparison of Toxicity of Anticancer Agents in Different Species

Freireich et al. analyzed toxicity data for 18 cancer chemotherapeutic drugs in six species, including mouse, rat, hamster, dog, monkey, and human. (Freireich et. al., Cancer Chemotherapy Rep. 50:219-244, 1966). On a mg/m$^2$ basis the toxic dose was approximately the same in each species. On a mg/kg basis the mouse dose was about 1/12 of the human. This relationship enables one to predict the effective human dose of a drug based on animal data, although there are exceptions and some drugs could show greater potency in one species versus another. Using the above relationship, the about 200 mg/kg oral dose of fluasterone in mouse translates into about 1200 mg daily in the human and about 5 mg/kg transdermal dose translates into about 28 mg human dose. The compositions herein can be formulated in the transdermal dosage range of about 0.01 mg/kg to about 100 mg/kg; preferably about 0.01 mg/kg to about 75 mg/kg; more preferably about 1 mg/kg to about 50 mg/kg. However, the daily dose can vary based on the animal and the medical condition being treated. For humans, the transdermal dosage can be in the ranges of about 0.01 to about 50 mg/kg, preferably, about 0.01 to about 25 mg/kg and more preferably, about 0.01 to about 10 mg/kg and even more preferably about 0.01 to about 5 mg/kg.

2. Estimation of Human Dose Based on Plasma Levels of Fluasterone Following Oral Administration to Humans or Mice An oral single dose PK experiment in mice following administration of 200 mg/kg fluasterone was performed. The calculated AUCO-24 was 2,242 (ngXh/mL). A PK study was also performed in 12 human volunteers as part of a phase I fluasterone study. The volunteers received either 800 mg or 1600 mg fluasterone orally as a daily dose. The AUCO-24/mg dose was calculated. The calculated AUCO-24 for the 1200 mg dose was 2,316 (ngXh/mL), which suggests that the 1200 mg human dose, as predicted by Freireich et al. (Supra), is bioequivalent to 200 mg/kg in the mouse.

3. Efficacy of Oral about 1200 mg Fluasterone Dose in Hypertriglyceridemic Patients The lowest effective oral dose of fluasterone which lowers fasting plasma triglycerides in diabetic mice is about 200 mg/kg, which translates into an oral human dose of about 1200 mg. In a phase I/II trial in hypertriglyceridemic patients we found that a dose of about 1200 mg significantly lowered fasting plasma triglyceride levels.

The data indicate that, as a reasonable guide, the approach of Freireich et al. can be used to predict human dose of fluasterone. Based on the efficacy of about 5 mg/kg administered transdermally to mice, a probable human dose range for transdermal delivery would be about 25 mg to about 50 mg.

EXAMPLES

Example 1

Solubility of Compounds of Formula I

Fluasterone: The solubility of fluasterone in various solvents was determined by adding a specific volume of solvent to a weighed amount of fluasterone in a screw-capped glass vial and shaking vigorously for several minutes. Incremental volumes of solvent were added, followed by vigorous shaking, until the fluasterone completely dissolved.

Alternatively solubility was determined by adding a specific volume of solvent to a weighed amount of fluasterone in a screw-capped glass vial and warming the vial on a hot plate with vigorous shaking until the fluasterone dissolved. Fluasterone was considered soluble if it remained in solution after at least a month at room temperature. Although the above procedures may not give precise solubilities, they should give a close approximation of maximum fluasterone solubility.

TABLE 2

| Fluasterone solubility | |
|---|---|
| Solvent | Solubility |
| Ethanol | 6.6 mg/mL |
| Polyethylene glycol 400 (PEG-400) | 1.1 mg/mL |
| Propylene glycol | >0.5 mg/mL |
| Limonene | 22.6 mg/mL |
| Dimethyl sulfoxide (DMSO) | 3.6 mg/mL |
| Isopropyl Myristate | 16 mg/mL |

Example 2

Solubility in Mixed Solvents

In these experiments fluasterone solubility was determined by adding fluasterone to a measured volume of solvent in a screw-capped glass vial. The vial was warmed on a hot plate with vigorous shaking until the fluasterone dissolved. Fluasterone was considered soluble if it remained in solution after at least a month at room temperature.

Solubility in 10% Tween 80-90% Ethanol (v/v): 21.4 mg of micronized fluasterone was weighed in a screw-capped glass vial and about 2.14 mL of a mixture of 10% Tween 80 (Sigma ultra) and 90% ethanol (ACS/USP grade) was added. The vial was warmed on a hot plate until the fluasterone dissolved. A few fine crystals of fluasterone were observed after standing 3 weeks at room temperature. Solubility is slightly less than 10 mg/mL.

Solubility in 15% Tween 80-85% Ethanol (v/v): 20.0 mg of micronized fluasterone was weighed in a screw-capped glass vial and 2.0 mL of a mixture of 15% Tween 80 and 85% ethanol added, and the vial was warmed on a hot plate until the fluasterone dissolved. A few fine crystals of fluasterone were observed after standing 3 weeks at room temperature. Solubility is slightly less than 10 mg/mL.

Solubility in 20% Tween 80-80% Ethanol (v/v): 18.5 mg of micronized fluasterone was weighed in a screw-capped glass vial and about 1.85 mL of a mixture of 20% Tween 80 and 80% ethanol was added. Fluasterone was dissolved by warming as described. The solution remained visibly clear after 2 months at room temperature. 28.5 mg of micronized fluasterone was weighed in a screw-capped glass vial and about 2.38 mL of a mixture of 20% Tween 80 and 80% ethanol was added (12 mg/mL). Fluasterone was dissolved by warming as described. After 3 days at room temperature some fluasterone crystals were seen. Solubility of fluasterone in 20% Tween 80 and 80% ethanol is greater than 10 mg/mL and less than 12 mg/mL.

Solubility in 50% Tween 80-50% Ethanol (v/v): 28.3 mg of micronized fluasterone was weighed in a screw-capped glass vial and 1.8 mL of a mixture of 50% Tween 80 and 50% ethanol was added (16 mg/mL). Fluasterone was dissolved by warming. A few crystals of fluasterone were observed after 1 month at room temperature. 28.8 mg of micronized fluasterone was weighed in a screw-capped glass vial and about 2.05 mL of a mixture of 50% Tween 80 and 50% ethanol was added (14 mg/mL). Fluasterone was dissolved by warming. After 7 weeks at room temperature the solution is visibly clear. Solubility is greater than 14 mg/mL and less than 16 mg/mL.

Solubility of Fluasterone in Cetyl Alcohol Ethanol (10%:90% w/w) Mixture: 29.9 mg of micronized fluasterone was weighed in a screw-capped glass vial and 3 mL of a mixture of 10% cetyl alcohol:90% ethanol added. The vial was warmed on a hot plate until the fluasterone dissolved. After 2 days at room temperature, some fluasterone crystals were seen. Solubility of fluasterone is somewhat less than 10 mg/mL.

Solubility of Fluasterone in Cetyl Alcohol:Ethanol (20%: 80% w/w) Mixture: 32.3 mg of micronized fluasterone was weighed in a screw-capped glass vial and 2.7 mL of 20% cetyl alcohol:80% ethanol was added (12 mg/mL). The vial was warmed on a hot plate until the fluasterone dissolved. After about 5 weeks at room temperature, a few small crystals of fluasterone were observed. Solubility of fluasterone is slightly less than 12 mg/mL. A solution of fluasterone (10 mg/mL) was also prepared in a mixture of 22% cetyl alcohol: 78% ethanol. After about 1 month at room temperature the solution was completely clear.

Solubility of fluasterone is greater than 10 mg/mL and less than 12 mg/mL, which is similar to Tween 80:ethanol mixtures.

Example 3

Dose-Response with Orally Administered Fluasterone on 12-O-tetradecanoylphorbol-13-acetate (TPA)-Induced DNA Synthesis in Mouse Epidermis In order to determine the lower range of effective oral dose of Fluasterone which abolishes 12-O-tetradecanoylphorbol-13-acetate (TPA)-stimulated epidermal hyperplasia in mouse skin the following experiment was performed.

Fluasterone suspensions were prepared using sesame oil as vehicle. Micronized fluasterone was obtained from Pharmaceutics International, Inc. Five suspensions were prepared— 100 mg/kg (13 mg/mL), 200 mg/kg (26.5 mg/mL), 400 mg/kg (52.4 mg/mL), 800 mg/kg (105.5 mg/mL), and 1200 mg/kg (158.3 mg/mL). The fluasterone for each suspension was weighed, placed into a plastic vial, and the required volume of sesame oil was added to the vial. The fluasterone was suspended in the sesame oil with the use of a Tekmar Tissumizer. Magnetic stirrer bars were added to the various suspensions which were stirred on a magnetic stirrer prior to treatment. Control and TPA groups received sesame oil alone.

Female CD-1 mice were obtained from Charles River Laboratories, Wilmington, Mass. at 35-37 days of age.

The mice were housed three per cage in plastic shoebox cages on Alphacel bedding with 12 hours of alternating light and dark in the CAF Animal Facility. The mice had ad libitum access to Purina 5015 chow and acidified tap water (pH≦2.6). The mice were shaved, weighed and distributed into groups of three.

Control

The mice were treated orally with 0.2 mL of sesame oil. One hour after treatment with sesame oil, the mice were treated topically with 0.2 mL of acetone.

TPA

The mice were treated orally with 0.2 mL of sesame oil. One hour after treatment with sesame oil, the mice were treated topically with 2 μg of TPA in 0.2 mL of acetone.

Fluasterone 100 mg/kg The mice were treated with 0.2 mL of a suspension of micronized fluasterone to give a dose of 100 mg/kg. One hour after treatment with fluasterone, the mice were treated topically with 2 μg of TPA in 0.2 mL of acetone.

Fluasterone 200 mg/kg The mice were treated with 0.2 mL of a suspension of micronized fluasterone to give a dose of 200 mg/kg. One hour after treatment with fluasterone, the mice were treated topically with 2 μg of TPA in 0.2 mL of acetone.

Fluasterone 400 mg/kg The mice were treated with 0.2 mL of a suspension of micronized fluasterone to give a dose of 400 mg/kg. One hour after treatment with fluasterone, the mice were treated topically with 2 μg of TPA in 0.2 mL of acetone.

Fluasterone 800 mg/kg The mice were treated with 0.2 mL of a suspension of micronized fluasterone to give a dose of 800 mg/kg. One hour after treatment with fluasterone, the mice were treated topically with 2 μg of TPA in 0.2 mL of acetone.

Fluasterone 1200 mg/kg The mice were treated with 0.2 mL of a suspension of micronized fluasterone to give a dose of 1200 mg/kg. One hour after treatment with fluasterone, the mice were treated topically with 2 μg of TPA in 0.2 mL of acetone.

The mice were sacrificed 20 hours after treatment by an overdose of $CO_2$. Twenty minutes prior to sacrifice, the mice were injected with 60 μCi of [$^3$H]thymidine (Amersham). The mice were treated with a depilatory to remove any residual hair. A 2×2 $cm^2$ piece of skin was excised, placed in ice water for 30 seconds, then in 55° C. water for 30 seconds, then in ice water again for 30 seconds. The epidermis was s raped off using a scalpel and the scrapings were placed into ice cold 0.4N TCA. The scrapings were homogenized using a Tekmar Tissumizer (80% power for 30 seconds). The homogenates were centrifuged for 20 minutes at 3,000×g. The precipitates were washed 3× with 0.2N TCA. The TCA was removed and the precipitates were stored at −20° C. overnight. The next day, the precipitates were washed 2× with absolute ethanol. The DNA in each sample was hydrolyzed with 0.5N TCA for 30 minutes at 90°. The tubes were centrifuged for 20 minutes at 3000×g. A 0.2 mL aliquot of each hydrolysate was counted in a LKB Rackbeta scintillation counter using Scintiverse II BD as the counting medium. DNA content was determined by the Burton diphenylamine assay.

Fluasterone Suspensions:

100 mg/kg: 26.0 mg was suspended in 2 mL of sesame oil) (13 mg/mL)

200 mg/kg: 61.0 mg was suspended in 2.3 mL of sesame oil (26.5 mg/mL)

400 mg/kg: 125.8 mg was suspended in 2.4 mL of sesame oil (52.4 mg/mL)

800 mg/kg: 211 mg was suspended in 2.0 mL of sesame oil (105.5 mg/mL)

1200 mg/kg: 316.6 mg was suspended in 2.0 mL of sesame oil (158.3 mg/mL)

TABLE 3

| Average body weights of mice | | | | | | |
| --- | --- | --- | --- | --- | --- | --- |
| Control | TPA | 100 mg/kg | 200 mg/kg | 400 mg/kg | 800 mg/kg | 1200 mg/kg |
| 25.5 ± 0.9 | 26.1 ± 1.0 | 26.5 ± 0.3 | 26.3 ± 0.4 | 26.2 ± 0.3 | 26.4 ± 0.3 | 26.4 ± 0.4 |

TABLE 4

Results of TPA induced DNA synthesis

|  | µg DNA | cpm/µg DNA |
|---|---|---|
| Group |  |  |
| Control | 4.7 ± 1.0 | 156.1 ± 33.6 |
| TPA | 14.1 ± 1.3 | 641.5 ± 115.2 |
| Fluasterone Groups: |  |  |
| 100 mg/kg | 15.5 ± 3.0 | 539.8 ± 75.9 |
| 200 mg/kg | 6.0 ± 1.9 | 185.0 ± 38.2 |
| 400 mg/kg | 6.6 ± 2.6 | 208.8 ± 144.2 |
| 800 mg/kg | 6.2 ± 1.0 | 634.3 ± 151.6 |
| 1200 mg/kg | 6.3 ± 1.5 | 850.0 ± 256.0 |

This experiment demonstrates that 200 mg/kg p.o. is the lowest tested dose which inhibits TPA-stimulated epidermal [$^3$H] thymidine incorporation (cpm/µg DNA) as well as the epidermal DNA content of a 2×2 cm$^2$ section of mouse skin (µg DNA). As the dose of fluasterone is increased, the cpm/µg DNA increases while the µg DNA value remains depressed. 200 mg/kg p.o. fluasterone is also the lowest effective dose which significantly lowers fasting plasma glucose and triglyceride levels in diabetic mice. As discussed in page 7, this is presumably from a decrease in the endogenous thymidine pool size as a consequence of G6PDH inhibition

Example 4

Dose Response Efficacy of Transdermally Administered Fluasterone in Inhibiting TPA-Stimulated Epidermal DNA Synthesis in Mouse Epidermis The solubility of fluasterone in various formulations have been tested for efficacy.

The following fluasterone solutions, and one suspension, have been tested in three TPA experiments.
1. A solution of fluasterone in carbitol at 12.7 mg/mL.
2. A solution of fluasterone in Cremophor EL (polyethoxylated castor oil) at 12.4 mg/mL.
3. A solution of fluasterone in a 50:50 mixture (v/v) of ethanol and Tween 80 at 10 mg/mL.
4. A solution of fluasterone in a 50:50 mixture (v/v) of ethanol and Cremophor EL at 10 mg/mL.
5. A solution of fluasterone in an 81:15:4 mixture of ethanol:R-(+)-limonene:isopropyl myristate (v/v/v) at 10 mg/mL.
6. A suspension of micronized fluasterone in a mixture of 76:19:5 ethanol:water:Tween-80 (v/v/v) at 10 mg/mL.

These solutions and one suspension have all suppressed TPA-stimulated epidermal [$^3$H] thymidine and epidermal DNA content at a dose of 2.5 mg/kg, which is the same potency of fluasterone following s.c. administration.

The Effect of Topically-Administered Fluasterone Dissolved in Either Carbitol or Cremophor EL on TPA-Induced DNA Synthesis in Mouse Epidermis:

This experiment demonstrates that transdermally applied fluasterone in solution in either carbitol or Cremophor EL, at a dose of 2.5 mg/kg, inhibits TPA-stimulated epidermal [$^3$H] thymidine incorporation (cpm/µg) as well as the epidermal DNA content of a 2×2 cm$^2$ section of mouse skin (µg DNA). This is the same potency seen with s.c.-injected fluasterone in this assay.

Treatment with the carbitol formulation produced a greater overshoot in [$^3$H] thymidine incorporation at 5 mg/kg (501±47.2 vs. 132±21.7), suggesting that fluasterone may be more bioavailable when dissolved in carbitol vs. Cremophor EL as the dose of fluasterone is increased.

Methods: Female CD-1 mice, 40-43 days old, were obtained from Charles River Laboratories, Kingston, N.Y. The mice were housed two per cage in plastic shoebox cages on Absorbdri bedding with 12 hours of alternating light and dark in the Central Animal Facility. The mice had ad libitum access to Purina 5015 chow and acidified tap water (pH≦2.6). The mice were allowed to acclimate to the facility for approximately two weeks prior to use in an experiment.

Micronized fluasterone was used. 24.1 mg of micronized fluasterone was weighed using a Mettler AE-50 balance, transferred to a glass scintillation vial, and dissolved in 1.9 mL of carbitol for the 5 mg/kg, 2.5 mg/kg, 1.9 mg/kg and 1.25 mg/kg fluasterone/carbitol groups. 23.6 mg of micronized fluasterone was weighed and dissolved in 1.9 mL of Cremophor EL for the 5 mg/kg, 2.5 mg/kg, 1.9 mg/kg and 1.25 mg/kg fluasterone/Cremophor EL groups.

The mice were weighed, marked with magic marker on the tail, and shaved on the back and the abdomen one day prior to treatment. Only those mice showing no hair regrowth were used in the experiment. Fluasterone was applied to the shaved abdomen one hour before TPA was applied to the shaved back. The mice were anesthetized and on their backs prior to topical application of TPA.

The mice were treated as follows, with two mice in each experimental group.

Carbitol Groups

Control: The mice were anesthetized with Isoflurane, and then were given an intramuscular injection of 0.1 ml solution of ketamine (50 mg/kg), xylazine (10 mg/kg) and atropine (0.1 mg/kg). Approximately 10 minutes after the i.m. Injection (after the mice could not turn over when placed on their backs), the mice were treated with 10 µL of carbitol. The mice were anesthetized and on their backs for approximately 30 minutes after application of carbitol. One hour after the application of carbitol, 0.2 ml of acetone was applied to the shaved area on the back of each mouse.

TPA: The mice were anesthetized with Isoflurane, and then were given an intramuscular injection of 0.1 mL solution of ketamine (50 mg/kg), xylazine (10 mg/kg) and atropine (0.1 mg/kg). Approximately 10 minutes after the i.m. injection (after the mice could not turn over when placed on their backs), the mice were treated with 10 µL of carbitol. The mice were anesthetized and on their backs for approximately 30 minutes after application of carbitol. One hour after the application of carbitol, 2 µg of TPA dissolved in 0.2 mL of acetone was applied to the shaved area on the back of each mouse.

5 mg/kg Fluasterone: The mice were anesthetized with Isoflurane, and then were given an intramuscular injection of 0.1 mL solution of ketamine (50 mg/kg), xylazine (10 mg/kg) and atropine (0.1 mg/kg). Approximately 10 minutes after the i.m. injection (after the mice could not turn over when placed on their backs), the mice were treated with 10 µL of a 12.5 mg/mL fluasterone/carbitol solution to give a dose of 5 mg/kg. The mice were anesthetized and on their backs for approximately 30 minutes after application of fluasterone/carbitol solution. One hour after the application of fluasterone/carbitol solution, 2 µg of TPA dissolved in 0.2 mL of acetone was applied to the shaved area on the back of each mouse.

2.5 mg/kg Fluasterone The mice were anesthetized with Isoflurane, and then were given an intramuscular injection of 0.1 mL solution of ketamine (50 mg/kg), xylazine (10 mg/kg) and atropine (0.1 mg/kg). Approximately 10 minutes after the i.m. injection (after the mice could not turn over when placed on their backs), the mice were treated with 5 µL of a 12.5 mg/mL fluasterone/carbitol solution to give a dose of 2.5 mg/kg. The mice were anesthetized and on their backs for approximately 30 minutes after application of fluasterone/carbitol solution. One hour after the application of fluasterone/carbitol solution, 2 µg of TPA dissolved in 0.2 mL of acetone was applied to the shaved area on the back of each mouse.

1.9 mg/kg Fluasterone The mice were anesthetized with Isoflurane, and then were given an intramuscular injection of 0.1 mL solution of ketamine (50 mg/kg), xylazine (10 mg/kg) and atropine (0.1 mg/kg). Approximately 10 minutes after the i.m. injection (after the mice could not turn over when placed on their backs), the mice were treated with 3.8 µL of a 12.5 mg/mL fluasterone/carbitol solution to give a dose of 1.9 mg/kg. The mice were anesthetized and on their backs for approximately 30 minutes after application of fluasterone/carbitol solution. One hour after the application of fluasterone/carbitol solution, 2 µg of TPA dissolved in 0.2 mL of acetone was applied to the shaved area on the back of each mouse.

1.25 mg/kg Fluasterone The mice were anesthetized with Isoflurane, and then were given an intramuscular injection of 0.1 mL solution of ketamine (50 mg/kg), xylazine (10 mg/kg) and atropine (0.1 mg/kg). Approximately 10 minutes after the i.m. injection (after the mice could not turn over when placed on their backs), the mice were treated with 2.5 µL of a 12.5 mg/mL fluasterone/carbitol solution to give a dose of 1.25 mg/kg. The mice were anesthetized and on their backs for approximately 30 minutes after application of fluasterone/carbitol solution. One hour after the application of fluasterone/carbitol solution, 2 µg of TPA dissolved in 0.2 mL of acetone was applied to the shaved area on the back of each mouse.

Cremophor EL Groups:

Control: The mice were anesthetized with Isoflurane, and then were given an intramuscular injection of 0.1 mL solution of ketamine (50 mg/kg), xylazine (10 mg/kg) and atropine (0.1 mg/kg). Approximately 10 minutes after the i.m. injection (after the mice could not turn over when placed on their backs), the mice were treated with 10 µL of Cremophor EL. The mice were anesthetized and on their backs for approximately 30 minutes after application of Cremophor EL. One hour after the application of Cremophor EL, 0.2 mL of acetone was applied to the shaved area on the back of each mouse.

TPA: The mice were anesthetized with Isoflurane, and then were given an intramuscular injection of 0.1 mL solution of ketamine (50 mg/kg), xylazine (10 mg/kg) and atropine (0.1 mg/kg). Approximately 10 minutes after the i.m. injection (after the mice could not turn over when placed on their backs), the mice were treated with 10 µL of Cremophor EL. The mice were anesthetized and on their backs for approximately 30 minutes after application of Cremophor EL. One hour after the application of Cremophor EL, 2 µg of TPA dissolved in 0.2 mL of acetone was applied to the shaved area on the back of each mouse.

5 mg/kg Fluasterone: The mice were anesthetized with Isoflurane, and then were given an intramuscular injection of 0.1 mL solution of ketamine (50 mg/kg), xylazine (10 mg/kg) and atropine (0.1 mg/kg). Approximately 10 minutes after the i.m. injection (after the mice could not turn over when placed on their backs), the mice were treated with 10 µL of a 12.5 mg/mL fluasterone/Cremophor EL solution to give a dose of 5 mg/kg. The mice were anesthetized and on their backs for approximately 30 minutes after application of fluasterone/Cremophor EL solution. One hour after the application of fluasterone/Cremophor EL solution, 2 µg of TPA dissolved in 0.2 mL of acetone was applied to the shaved area on the back of each mouse.

2.5 mg/kg Fluasterone: The mice were anesthetized with Isoflurane, and then were given an intramuscular injection of 0.1 mL solution of ketamine (50 mg/kg), xylazine (10 mg/kg) and atropine (0.1 mg/kg). Approximately 10 minutes after the i.m. injection (after the mice could not turn over when placed on their backs), the mice were treated with 5 µL of a 12.5 mg/mL fluasterone/Cremophor EL solution to give a dose of 2.5 mg/kg. The mice were anesthetized and on their backs for approximately 30 minutes after application of fluasterone/Cremophor EL solution. One hour after the application of fluasterone/Cremophor EL solution, 2 µg of TPA dissolved in 0.2 mL of acetone was applied to the shaved area on the back of each mouse.

1.9 mg/kg Fluasterone: The mice were anesthetized with Isoflurane, and then were given an injection of 0.1 mL solution of ketamine (50 mg/kg), xylazine (10 mg/kg) and atropine (0.1 mg/kg). Approximately 10 minutes after the i.m. injection (after the mice could not turn over when placed on their backs), the mice were treated with 3.8 µL of a 12.5 mg/mL fluasterone/Cremophor EL solution to give a dose of 1.9 mg/kg. The mice were anesthetized and on their backs for approximately 30 minutes after application of fluasterone/Cremophor EL solution. One hour after the application of fluasterone/Cremophor EL solution, 2 µg of TPA dissolved in 0.2 mL of acetone was applied to the shaved area on the back of each mouse.

1.25 mg/kg Fluasteorne: The mice were anesthetized with Isoflurane, and then were given an intramuscular injection of 0.1 mL solution of ketamine (50 mg/kg), xylazine (10 mg/kg) and atropine (0.1 mg/kg). Approximately 10 minutes after the i.m. injection (after the mice could not turn over when placed on their backs), the mice were treated with 2.5 µL of a 12.5 mg/mL fluasterone/Cremophor EL solution to give a dose of 1.25 mg/kg. The mice were anesthetized and on their backs for approximately 30 minutes after application of fluasterone/Cremophor EL solution. One hour after the application of fluasterone/Cremophor EL solution, 2 µg of TPA dissolved in 0.2 mL of acetone was applied to the shaved area on the back of each mouse.

The mice were sacrificed 20 hours after treatment by an overdose of $CO_2$. Twenty minutes prior to sacrifice, the mice were injected with 60 µCi of [$^3$H] thymidine). The mice were treated with a depilatory to remove any residual hair. A piece of skin (approximately 2×2 $cm^2$) was excised, placed in ice water for 30 seconds, then in 55° water for 30 seconds, then in ice water again for 30 seconds. The epidermis was scraped off using a scalpel and the scrapings were placed into ice cold 0.4N TCA. The scrapings were homogenized using a Tekmar Tissumizer (80% power for 30 seconds). The homogenates were centrifuged for 20 minutes at 3000×g. The precipitates were washed 4× with 0.2N TCA, and 2× with absolute ethanol. The DNA was hydrolyzed with 0.5N TCA for 30 minutes at 90°. The tubes were centrifuged for 20 minutes at 3000×g. 0.2 mL aliquots of the supernatants were counted in an LKB 1209 Rackbeta scintillation counter, using Scintiverse BD as counting medium. DNA content was determined by the Burton diphenylamine assay.

TABLE 5

Body weight of mice in the carbitol group

| Control | TPA | 5 mg/kg | 2.5 mg/kg | 1.9 mg/kg | 1.25 mg/kg |
|---|---|---|---|---|---|
| 26.0 ± 0.5 | 24.8 ± 0.2 | 25.8 ± 0.4 | 25.5 ± 0.2 | 25.3 ± 0.2 | 25.3 ± 0.4 |

TABLE 6

Body weight of mice in the Cremophor EL group

| Control | TPA | 5 mg/kg | 2.5 mg/kg | 1.9 mg/kg | 1.25 mg/kg |
|---|---|---|---|---|---|
| 26.0 ± 0.4 | 25.4 ± 0.6 | 25.3 ± 0.1 | 25.6 ± 0.1 | 25.6 ± 0.1 | 25.4 ± 0.0 |

TABLE 7

Effect of fluasterone on TPA-induced DNA synthesis

| Group | cpm | µg DNA/0.2 mL | corrected cpm | cpm/µg DNA |
|---|---|---|---|---|
| Carbitol Groups | | | | |
| Control | 606 | 8.6 | 571 | 66.4 |
|  | 461 | 9.1 | 426 | 46.8 |
|  |  |  |  | 56.6 ± 13.9 |
| TPA | 6,764 | 20.3 | 6,729 | 331.5 |
|  | 7,531 | 21.2 | 7,496 | 353.6 |
|  |  |  |  | 342.6 ± 15.6 |
| 5 mg/kg | 5,373 | 10.0 | 5,338 | 533.8 |
|  | 5,080 | 10.8 | 5,045 | 467.1 |
|  |  |  |  | 500.5 ± 47.2 |
| 2.5 mg/kg | 651 | 9.5 | 616 | 64.8 |
|  | 684 | 8.8 | 649 | 73.8 |
|  |  |  |  | 69.3 ± 6.3 |
| 1.9 mg/kg | 6,767 | 18.4 | 6,732 | 365.9 |
|  | 2,722 | 11.8 | 2,687 | 227.7 |
|  |  |  |  | 296.8 ± 97.7 |
| 1.25 mg/kg | 6,086 | 22.4 | 6,051 | 270.1 |
|  | 10,205 | 29.8 | 10,170 | 341.3 |
|  |  |  |  | 287.9 ± 25.2 |
| Cremophor EL Groups | | | | |
| Control | 903 | 8.7 | 868 | 99.8 |
|  | 782 | 8.5 | 747 | 87.9 |
|  |  |  |  | 93.9 ± 8.4 |
| TPA | 16,877 | 28.7 | 16,842 | 586.8 |
|  | 13,884 | 30.4 | 13,849 | 455.6 |
|  |  |  |  | 521.2 ± 92.8 |
| 5 mg/kg | 1,015 | 8.4 | 980 | 116.7 |
|  | 1,686 | 11.2 | 1,651 | 147.4 |
|  |  |  |  | 132.1 ± 21.7 |
| 2.5 mg/kg | 590 | 8.6 | 555 | 64.5 |
|  | 1,359 | 10.1 | 1,324 | 131.1 |
|  |  |  |  | 97.8 ± 47.1 |
| 1.9 mg/kg | 2,514 | 15.4 | 2,479 | 161.0 |
|  | 5,468 | 20.1 | 5,433 | 270.3 |
|  |  |  |  | 215.7 ± 77.3 |
| 1.25 mg/kg | 14,290 | 28.1 | 14,255 | 507.3 |
|  | 6,208 | 14.9 | 6,173 | 414.3 |
|  |  |  |  | 460.1 ± 65.8 |

Example 5

The Effect of Topically Applied-Fluasterone Dissolved in Either Cremophor EL:ethanol (50:50 v/v) or Tween 80:Ethanol (50:50 v/v) on TPA-Induced DNA Synthesis in Mouse Epidermis In the Tween 80:ethanol group, a dose of 2.5 mg/kg suppressed the TPA-stimulated increase in epidermal DNA content (µg DNA). With respect to [$^3$H] thymidine incorporation (cpm/µg DNA), the 2.5 mg/kg dose suppressed this value in 1 of 3 mice, whereas the other 2 mice showed the artifactual increase. The lowest effective dose is about 2.5 mg/kg or somewhat lower.

In the Cremophor EL:ethanol group, treatment with this formulation greatly enhanced the effect of TPA in stimulating [$^3$H] thymidine incorporation and epidermal DNA content when compared to the Tween 80:ethanol group. Cremophor EL had been used to formulate the drug paclitaxel for i.v. administration and is believed to cause acute hypersensitivity reactions. Cremophor EL has been replaced by Tween-80 to formulate paclitaxel. As such, Cremophor EL may not be the best solvent for formulating fluasterone.

Methods: Female CD-1 mice, 40-43 days old, were obtained from Charles River Laboratories, Kingston, N.Y. The mice were housed two per cage in plastic shoebox cages on Absorbdri bedding with 12 hours of alternating light and dark. The mice had ad libitum access to Purina 5015 chow and acidified tap water (pH≦2.6). The mice were allowed to acclimate to the facility for approximately one week prior to use in an experiment.

Micronized 8354 was used. 34.1 mg of micronized 8354 was weighed using a Mettler AE-50 balance, transferred to a glass scintillation vial, and dissolved in 3.4 mL of Cremophor EL:ethanol (50:50 v/v) for the 5 mg/kg, 2.5 mg/kg, and 1.9 mg/kg fluasterone:Cremophor EL:ethanol groups. 32.1 mg of micronized fluasterone was weighed and dissolved in 3.2 mL of Tween 80:ethanol solution (50:50, v/v) for the 5 mg/kg, 2.5 mg/kg, and 1.9 mg/kg fluasterone:Tween 80:ethanol groups.

The mice were weighed, marked with magic marker on the tail, and shaved on the back and the abdomen two days prior to treatment. Only those mice showing no hair regrowth were used in the experiment.

The mice were treated as follows, with two mice in each experimental group

Cremophor EL:Ethanol Groups:

Control: The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 12.5 µL of Cremophor EL:ethanol vehicle. The mice were anesthetized and on their backs for approximately 30 minutes after application of Cremophor EL:ethanol vehicle. One hour after the application of Cremophor EL:ethanol solution, 0.2 mL of acetone was applied to the shaved area on the back of each mouse.

TPA: The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 12.5 µL of Cremophor EL:ethanol solution. The mice were anesthetized and on their backs for approximately 30 minutes after application of Cremophor EL:ethanol solution. One hour after the application of Cremophor EL:ethanol solution, 2 µg of TPA dissolved in 0.2 mL of acetone was applied to the shaved area on the back of each mouse.

5 mg/kg Fluasterone The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 12.5 µL of a 10 mg/mL fluasterone:Cremophor EL:ethanol solution to give a dose of 5 mg/kg. The mice were anesthetized and on their backs for approximately 30 minutes after application of Cremophor EL:ethanol solution. One hour after the application of Cremophor EL:ethanol solution, 2 µg of TPA dissolved in 0.2 mL of acetone was applied to the shaved area on the back of each mouse.

2.5 mg/kg Fluasterone The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 6.25 µL of a 10 mg/mL fluasterone:Cremophor EL:ethanol solution to give a dose of 2.5 mg/kg. The mice were anesthetized and on their backs for approximately 30 minutes after application of Cremophor EL:ethanol solution. One hour after the application of Cremophor EL:ethanol solution, 2 µg of TPA dissolved in 0.2 mL of acetone was applied to the shaved area on the back of each mouse.

1.9 mg/kg Fluasterone The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 4.8 µL of a 10 mg/mL fluasterone:Cremophor EL:ethanol solution to give a dose of 1.9 mg/kg. The mice were anesthetized and on their backs for approximately 30 minutes after application of Cremophor EL:ethanol solution. One hour after the application of Cremophor EL:ethanol solution, 2 µg of TPA dissolved in 0.2 mL of acetone was applied to the shaved area on the back of each mouse.

Tween-80/Ethanol Groups:

Control: The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 12.5 µL of Tween 80:ethanol solution. The mice were anesthetized and on their backs for approximately 30 minutes after application of Tween 80:ethanol. One hour after the application of Tween 80:ethanol, 0.2 mL of acetone was applied to the shaved area on the back of each mouse.

TPA: The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 12.5 µL of Tween 80:ethanol solution. The mice were anesthetized and on their backs for approximately 30 minutes after application of Tween 80:ethanol solution. One hour after the application of Tween 80:ethanol, 2 µg of TPA dissolved in 0.2 mL of acetone was applied to the shaved area on the back of each mouse.

5 mg/kg Fluasterone The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 12.5 µL of a 10 mg/mL fluasterone:Tween 80:ethanol solution to give a dose of 5 mg/kg. The mice were anesthetized and on their backs for approximately 30 minutes after application of Tween 80:ethanol solution. One hour after the application of Tween 80:ethanol solution, 2 µg of TPA dissolved in 0.2 mL of acetone was applied to the shaved area on the back of each mouse.

2.5 mg/kg Fluasterone The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 6.25 µL of a 10 mg/mL fluasterone:Tween 80:ethanol solution to give a dose of 2.5 mg/kg. The mice were anesthetized and on their backs for approximately 30 minutes after application of Tween 80:ethanol solution. One hour after the application of Tween 80:ethanol solution, 2 µg of TPA dissolved in 0.2 mL of acetone was applied to the shaved area on the back of each mouse.

1.9 mg/kg Fluasterone The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 4.8 µL of a 10 mg/mL fluasterone:Tween 80:ethanol solution to give a dose of 1.9 mg/kg. The mice were anesthetized and on their backs for approximately 30 minutes after application of Tween 80:ethanol solution. One hour after the application of Tween 80:ethanol solution, 2 µg of TPA dissolved in 0.2 mL of acetone was applied to the shaved area on the back of each mouse.

The mice were sacrificed 20 hours after treatment by an overdose of $CO_2$. Twenty minutes prior to sacrifice, the mice were injected with 60 µCi of [$^3$H] thymidine. The mice were treated with a depilatory to remove any residual hair. A piece of skin (approximately 2×2 $cm^2$) was excised, placed in ice water for 30 seconds, then in 55° water for 30 seconds, then in ice water again for 30 seconds. The epidermis was scraped off using a scalpel and the scrapings were placed into ice cold 0.4N TCA. The scrapings were homogenized using a Tekmar Tissumizer (80% power for 30 seconds). The homogenates were centrifuged for 20 minutes at 3000×g. The precipitates were washed 4× with 0.2N TCA, and 2× with absolute ethanol. The DNA was hydrolyzed with 0.5N TCA for 30 minutes at 90°. The tubes were centrifuged for 20 minutes at 3000×g. 0.2 mL aliquots of the supernatants were counted in an LKB 1209 Rackbeta scintillation counter, using Scintiverse BD as counting medium. DNA content was determined by the Burton diphenylamine assay.

TABLE 8

Body weight of mice in the cremophor EL:ethanol solution Groups

| Control | TPA | 5 mg/kg | 2.5 mg/kg | 1.9 mg/kg |
|---|---|---|---|---|
| 23.5 ± 0.2 | 24.3 ± 0.1 | 23.3 ± 0.2 | 23.5 ± 0.4 | 23.8 ± 0.5 |

TABLE 9

Body weight of mice in the Tween 80:ethanol solution solution groups

| Control | TPA | 5 mg/kg | 2.5 mg/kg | 1.9 mg/kg |
|---|---|---|---|---|
| 24.0 ± 0.4 | 23.6 ± 0.9 | 23.4 ± 0.4 | 23.3 ± 0.4 | 23.6 ± 0.1 |

TABLE 10

Effect of fluasterone on TPA-induced DNA synthesis

| Group | cpm | µg DNA/0.2 | corrected cpm | cpm/µg DNA |
|---|---|---|---|---|
| Cremophor EL:ethanol Groups | | | | |
| Control | 2,596 | 10.0 | 2,571 | 257.1 |
|  | 670 | 11.6 | 645 | 55.6 |
|  |  |  |  | 156.4 ± 142.5 |
| TPA | 54,343 | 35.7 | 54,308 | 1,521.2 |
|  | 54,744 | 36.9 | 54,709 | 1,482.6 |
|  |  |  |  | 1,501.9 ± 27.3 |
| 1.9 mg/kg | 5,990 | 28.7 | 5,965 | 207.8 |
|  | 4,050 | 25.1 | 4,025 | 160.4 |
|  |  |  |  | 187.1 ± 33.5 |
| 2.5 mg/kg | 7,093 | 16.7 | 7,068 | 423.2 |
|  | 6,268 | 15.2 | 6,243 | 410.7 |
|  | 6,366 | 13.7 | 6,341 | 462.8 |
|  |  |  |  | 432.2 ± 27.2 |
| 5 mg/kg | 1,902 | 15.0 | 1,877 | 125.1 |
|  | 3,145 | 14.0 | 3,120 | 222.9 |
|  | 2,770 | 13.3 | 2,745 | 206.4 |
|  |  |  |  | 184.8 ± 52.4 |
| Tween/Ethanol Groups | | | | |
| Control | 327 | 5.4 | 302 | 55.9 |
|  | 673 | 6.2 | 648 | 104.5 |
|  |  |  |  | 80.2 ± 34.4 |
| TPA | 4,301 | 17.5 | 4,276 | 244.3 |
|  | 3,139 | 18.6 | 3,114 | 167.4 |
|  |  |  |  | 205.9 ± 54.4 |
| 1.9 mg/kg | 3,139 | 14.4 | 3,114 | 216.3 |
|  | 3,175 | 16.6 | 3,150 | 189.8 |
|  |  |  |  | 203.1 ± 18.7 |
| 2.5 mg/kg | 670 | 7.0 | 645 | 92.1 |
|  | 1,912 | 7.5 | 1,887 | 251.6 |
|  | 1,700 | 7.9 | 1,675 | 212.0 |
|  |  |  |  | 185.2 ± 83.0 |
| 5 mg/kg | 1,716 | 7.8 | 1,691 | 216.8 |
|  | 1,631 | 4.8 | 1,606 | 334.6 |
|  | 2,561 | 4.6 | 2,536 | 551.3 |
|  |  |  |  | 367.6 ± 169.7 |

In the Cremophor EL:ethanol group, treatment with this formulation greatly enhanced the effect of TPA in stimulating [$^3$H] thymidine incorporation and epidermal DNA content when compared to the Tween 80:ethanol group. Cremophor EL had been used to formulate the drug paclitaxel for i.v. administration and is believed to cause acute hypersensitivity reactions, which may account for the enhanced TPA effect with Cremophor EL in this experiment. Cremophor EL has been replaced by Tween-80 to formulate paclitaxel.

Example 6

The Effect of Topically Applied Fluasterone Dissolved in Ethanol:Limonene:Isopropyl Myristate (81:15:4 v/v/v) or a Suspension of Micronized Fluasterone in Ethanol:Water:Tween 80 (76:19:5 v/v/v) on TPA-Induced DNA Synthesis in Mouse Epidermis Topical compositions of fluasterone with gel-like consistency were prepared by the addition of carbomer 940 and triethanolamine to a suspension of micronized fluasterone in a mixture of ethanol:water:Tween 80.

Both formulations suppress TPA-stimulated-epidermal DNA content per 2×2 cm$^2$ of skin at a dose of 2.5 mg/kg. In the fluasterone-solution group, one of two mice in the 2.5 mg/kg dose group and both in the 5 mg/kg group showed the typical artifactual increase in [$^3$H] thymidine cpm/µg DNA. In the fluasterone-suspension group one mouse in the 5 mg/kg group showed this increase.

The data indicate that transdermal application of the fluasterone-suspension formulation is about as active as s.c. administration in suppressing TPA-stimulated epidermal hyperplasia. The fluasterone-ethanol-limonene-isopropyl myristate solution is slightly more active.

Methods and Results

Fluasterone Solution

The following were added to two separate glass scintillation vials:
  8.2 mL absolute ethanol (PharmCo, ACS/USP Grade)
  1.5 mL R+ limonene (Aldrich, 94%)
  0.4 mL isopropyl myristate (Sigma, 98%)

To one scintillation vial 101.2 mg of micronized fluasterone was added. Upon vigorous shaking for a few minutes and fluasterone was dissolved. The other vial was used to treat Control and TPA-without-fluasterone mice.

Fluasterone Suspension

The following were added to two separate glass scintillation vials:
  8 mL absolute ethanol (PharmCo, ACS/USP Grade)
  2 mL double distilled water
  0.5 mL Tween 80 (Sigma, ultra pure)

105.4 mg of micronized fluasterone was added to one vial. The suspension was sonicated with a Tekmar Tissumizer at a high setting of for approximately three minutes. The non-fluasterone mixture was used for Control and TPA-without-fluasterone mice.

Treatment of Mice

Female CD-1 mice, 40-43 days old, were obtained from Charles River Laboratories, Kingston, N.Y. The mice were housed five per cage in plastic shoebox cages on Betachip bedding with 12 hours of alternating light and dark in the Central Animal Facility. The mice had ad libitum access to Purina 5015 chow and acidified tap water (pH 2.6). The mice remained in the Animal Facility for approximately one month.

The mice were shaved on the back and the abdomen one day prior to treatment. Only those mice showing no hair regrowth were used in the experiment. The age of the mice at the time of the experiment was approximately 79 days of age. The usual age of mice used in prior experiments was approximately 50 days of age.

The mice were treated as follows, with two mice in each experimental group.

Control: The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 12.3 µL of ethanol:limonene:isopropyl myristate vehicle on the abdomen. The mice were anesthetized and on their backs for approximately 30 minutes after application of vehicle. One hour after the application of ethanol:limonene:isopropyl myristate solution, 0.2 mL of acetone was applied to the shaved area on the back of each mouse.

TPA: The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 12.3 µL of ethanol:limonene:isopropyl myristate solution. The mice were anesthetized and on their backs for approximately 30 minutes after application of vehicle. One hour after the application of ethanol:limonene:isopropyl myristate solution, 2 µg of TPA dissolved in 0.2 mL of acetone was applied to the shaved area on the back of each mouse.

1.5 mg/kg Fluasterone: The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 3.7 µL of a 10 mg/mL fluasterone:ethanol:limonene:isopropyl myristate solution to give a dose of 1.5 mg/kg. The mice were anesthetized and on their backs for approximately 30 minutes after application of fluasterone:ethanol:limonene:isopropyl myristate solution. One hour after the application of fluasterone solution, 2 µg of TPA dissolved in 0.2 mL of acetone was applied to the shaved area on the back of each mouse.

2.5 mg/kg Fluasterone The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 6.2 µL of a 10 mg/mL fluasterone:ethanol:limonene:isopropyl myristate solution to give a dose of 2.5 mg/kg. The mice were anesthetized and on their backs for approximately 30 minutes after application of fluasterone:ethanol:limonene:isopropyl myristate solution. One hour after the application of fluasterone solution, 2 µg of TPA dissolved in 0.2 mL of acetone was applied to the shaved area on the back of each mouse.

5 mg/kg Fluasterone The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 12.3 µL of a 10 mg/mL fluasterone/ethanol:limonene:isopropyl myristate solution to give a dose of 5 mg/kg. The mice were anesthetized and on their backs for approximately 30 minutes after application of fluasterone:ethanol:limonene:isopropyl myristate solution. One hour after the application of fluasterone solution, 2 µg of TPA dissolved in 0.2 mL of acetone was applied to the shaved area on the back of each mouse.

Control: The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 12.3 µL of ethanol:water:Tween 80 solution on the abdomen. The mice were anesthetized and on their backs for approximately 30 minutes after application of vehicle. One hour after the application of ethanol:water:Tween 80, 0.2 mL of acetone was applied to the shaved area on the back of each mouse.

TPA: The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 12.3 µL of ethanol:water:Tween 80 solution. The mice were anesthetized and on their backs for approximately 30 minutes after application of vehicle. One hour after the application of ethanol:water:Tween 80, 2 µg of TPA dissolved in 0.2 mL of acetone was applied to the shaved area on the back of each mouse.

1.5 mg/kg Fluasterone The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 3.7 µL of a 10 mg/mL fluasterone:ethanol:water:Tween 80 suspension to give a dose of 1.5 mg/kg. The mice were anesthetized and on their backs for approximately 30 minutes after application of fluasterone suspension. One hour after the application of the fluasterone suspension, 2 µg of TPA dissolved in 0.2 mL of acetone was applied to the shaved area on the back of each mouse.

2.5 mg/kg Fluasterone The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 6.2 µL of a 10 mg/mL fluasterone:ethanol:water:Tween 80 suspension to give a dose of 2.5 mg/kg. The mice were anesthetized and on their backs for approximately 30 minutes after application of fluasterone suspension. One hour after the application of the fluasterone suspension, 2 µg of TPA dissolved in 0.2 mL of acetone was applied to the shaved area on the back of each mouse.

5 mg/kg Fluasterone The mice were anesthetized with Isoflurane, and then were given an intramuscular injection of 0.1 mL solution of ketamine (50 mg/kg) and xylazine (10 mg/kg). Approximately 10 minutes after the i.m. injection (after the mice could not turn over when placed on their backs), the mice were treated with 12.3 µL of a 10 mg/mL fluasterone:ethanol:water:Tween 80 suspension to give a dose of 5 mg/kg. The mice were anesthetized and on their backs for approximately 30 minutes after application of fluasterone suspension. One hour after the application of the fluasterone suspension, 2 µg of TPA dissolved in 0.2 mL of acetone was applied to the shaved area on the back of each mouse.

The mice were sacrificed 20 hours after treatment by an overdose of $CO_2$. Twenty minutes prior to sacrifice, the mice were injected with 60 µCi of [$^3$H] thymidine. The mice were treated with a depilatory to remove any residual hair. A piece of skin (approximately 2×2 $cm^2$) was excised, placed in ice water for 30 seconds, then in 55° water for 30 seconds, then in ice water again for 30 seconds. The epidermis was scraped off using a scalpel and the scrapings were placed into ice cold 0.4N TCA. The scrapings were homogenized using a Tekmar Tissumizer (80% power for 30 seconds). The homogenates were centrifuged for 20 minutes at 3000×g. The precipitates were washed 4× with 0.2N TCA, and 2× with absolute ethanol. The DNA was hydrolyzed with 0.5N TCA for 30 minutes at 90°. The tubes were centrifuged for 20 minutes at 3000×g. 0.2 mL aliquots of the supernatants were counted in an LKB 1209 Rackbeta scintillation counter, using Scintiverse BD as counting medium. DNA content was determined by the Burton diphenylamine assay.

TABLE 11

Effect of fluasterone on TPA-induced DNA synthesis

| Group | cpm | µg DNA/0.2 mL | corrected cpm | cpm/µg DNA |
|---|---|---|---|---|
| Ethanol:Limonene:Isopropyl Myristate Groups | | | | |
| Control | 3,625 | 20.6 | 3,596 | 174.6 |
| | 2,583 | 18.7 | 2,554 | 136.6 |
| | | 19.7 ± 1.34 | | 155.6 ± 26.9 |
| TPA | 11,138 | 34.5 | 11,109 | 322.0 |
| | 8,574 | 30.8 | 8,545 | 277.4 |
| | | 32.7 ± 2.61 | | 299.7 ± 31.5 |
| 1.5 mg/kg | 5,883 | 25.8 | 5,854 | 226.9 |
| | 3,732 | 25.1 | 3,703 | 147.5 |
| | | 25.5 ± 0.50 | | 187.2 ± 56.1 |
| 2.5 mg/kg | 3,453 | 18.1 | 3,424 | 189.2 |
| | 7,109 | 15.3 | 7,080 | 462.7 |
| | | 16.7 ± 1.98[1] | | 326.0 ± 193 |
| 5 mg/kg | 8,496 | 15.9 | 8,467 | 532.5 |
| | 10,465 | 17.3 | 10,436 | 603.2 |
| | | 16.6 ± 0.99[1] | | 567.9 ± 50 |
| Ethanol:Water:Tween 80 Groups | | | | |
| Control | 2,327 | 18.3 | 2,298 | 125.6 |
| | 1,662 | 23.7 | 1,633 | 68.9 |
| | | 21.0 ± 3.82 | | 97.3 ± 40.1 |
| TPA | 7,303 | 34.9 | 7,274 | 208.4 |
| | 6,586 | 35.2 | 6,557 | 186.3 |
| | | 35.1 ± 0.21 | | 197.4 ± 15.6 |
| 1.5 mg/kg | 4,684 | 34.3 | 4,655 | 135.7 |
| | 3,510 | 35.2 | 3,481 | 98.9 |
| | | 34.8 ± 0.64 | | 117.3 ± 26.0 |
| 2.5 mg/kg | 2,176 | 19.6 | 2,147 | 109.5 |
| | 2,337 | 16.6 | 2,308 | 139.0 |
| | | 18.1 ± 2.1[2] | | 124.3 ± 20.9 |

TABLE 11-continued

Effect of fluasterone on TPA-induced DNA synthesis

| Group | cpm | µg DNA/0.2 mL | corrected cpm | cpm/µg DNA |
|---|---|---|---|---|
| 5 mg/kg | 2,713 | 16.5 | 2,684 | 162.7 |
|  | 7,718 | 18.9 | 7,689 | 406.8 |
|  |  | 17.7 ± 1.7[3] |  | 284.8 ± 173 |

Significantly less than corresponding TPA group.
[1]$p < 0.05$,
[2]$p < 0.02$,
[3]$p < 0.01$ Example 7

Effect of Dehydroepiandrosterone and Fluasterone on Dexamethasone-Induced Thymic and Splenic Atrophy Administration of dehydroepiandrosterone (DHEA, 60 mg/kg, s.c.) for three days partially reverse thymic and splenic atrophy induced by a single injection of dexamethasone (1.6 mg/mouse). In this experiment, the efficacy of either 10 mg/kg or 20 mg/kg DHEA administered s.c. versus the effect of 10 mg/kg or 20 mg/kg fluasterone was investigated.

Example 1

Efficacy of Subcutaneous Injection of Fluasterone Against Thymic and Splenic Atrophy Cremophor-saline vehicle: 5% Cremophor (polyethoxylated castor oil; Sigma Chemicals)-95% saline vehicle was prepared using 95 mL of sterile 0.9% NaCl (filtered through sterile 0.22 micron filter) and 5 mL of Cremophor. The Cremophor was dissolved by swirling for approximately 5 minutes.
Dexamethasone: Dexamethasone solutions were prepared by dissolving dexamethasone (Sigma Chemicals) in absolute ethanol. For example, 71.9 mg of dexamethasone was dissolved in 2.9 mL of absolute ethanol. In order to prevent precipitation, the solution was kept on a hotplate between injections.
For the 10 mg/kg suspension, 25.7 mg of DHEA was weighed out, transferred to a glass scintillation vial, and 10.3 mL of the Cremophor-saline vehicle was added. The DHEA suspension was homogenized using a Tissumizer at 80% power for 30 sec. The Tissumizer was rinsed with 70% ethanol prior to homogenization. After the 10 mg/kg DHEA suspension was homogenized the probe was rinsed 2x with 50 mL of absolute ethanol, then with 50 mL of 70% ethanol, and then dried with sterile gauze. For the 20 mg/kg DHEA suspension, 50.9 mg DHEA was suspended in 10.2 mL of Cremophor-saline vehicle.
The probe was then washed with detergent, rinsed with 500 mL deionized water, 5x, rinsed with 70% ethanol, and then the probe was dried with a sterile gauze pad prior to homogenizing the 10 mg/kg fluasterone suspension.
19.4 mg of fluasterone was weighed out and transferred to a glass scintillation vial. 7.8 mL of Cremophor-saline vehicle was added to the vial and the contents of the vial were homogenized with a Tissumizer as described previously. Prior to preparing the 20 mg/kg fluasterone, the probe was rinsed 2x with 50 mL of absolute ethanol and 1x with 50 mL of 70% ethanol. For the 20 mg/kg suspension, 47.0 mg was weighed out and transferred to a glass scintillation vial. 9.4 mL of Cremophor-saline vehicle was added to the vial and the contents of the vial were homogenized with a Tissumizer as described above.
Mice: Female CD-1 mice, 43-45 days old, were obtained from Charles River Laboratories. The mice were housed 5 per cage in plastic shoebox cages with ad libitum access to Purina chow 5015 and water in the Pharmacy CAF with 12 hr of alternating light and darkness.
Pretreatment with DHEA or fluasterone: Prior to the experiment the mice were weighed, separated into 6 groups containing 5 mice each and treated as follows:
Control: Mice were treated s.c. with 0.1 mL of 5% Cremophor-95% saline for three days. On the third day, the mice were also treated s.c. with 0.06 mL of absolute ethanol.
Dexamethasone: Mice were treated s.c. with 0.1 mL of 5% Cremophor-95% saline for three days. On the third day, the mice were also treated s.c. with 1.6 mg of dexamethasone dissolved in 0.06 mL of absolute ethanol.
10 mg/kg DHEA: Mice were treated s.c. with 0.25 mg of DHEA suspended in 0.1 mL of 5% Cremophor-95% saline for three days. On the third day, the mice were also treated s.c. with 1.6 mg of dexamethasone dissolved in 0.06 mL of absolute ethanol.
20 mg/kg DHEA: Mice were treated s.c. with 0.5 mg of DHEA suspended in 0.1 mL of 5% Cremophor-95% saline for three days. On the third day, the mice were also treated s.c. with 1.6 mg of dexamethasone dissolved in 0.06 mL of absolute ethanol.
10 mg/kg Fluasterone: Mice were treated s.c. with 0.25 mg of fluasterone suspended in 0.1 mL of 5% Cremophor-95% saline for three days. On the third day, the mice were also treated s.c. with 1.6 mg of dexamethasone dissolved in 0.06 mL of absolute ethanol.
20 mg/kg Fluasterone: Mice were treated s.c. with 0.5 mg of fluasterone suspended in 0.1 mL of 5% Cremophor-95% saline for three days. On the third day, the mice were also treated s.c. with 1.6 mg of dexamethasone dissolved in 0.06 mL of absolute ethanol.
All s.c. injections were made in the nape. All mice were lightly anesthetized while the s.c. injections were done.
Twenty-four hours after dexamethasone treatment, the mice were euthanized by an overdose of isoflurane. The spleen and thymus were removed, cleaned of any adventitia, rinsed, blotted on filter paper, and weighed.

TABLE 12

Average thymus and spleen weights after euthanization

| Group | Body Weight | Thymus wt. | Thymus wt/BW | Spleen wt | Spleen wt/BW |
|---|---|---|---|---|---|
| CONTROL | 24.6 ± 0.9 | 69.6 ± 8.8 | 2.8 ± 0.4 | 91.7 ± 7.4 | 3.7 ± 0.2 |
| DEXAMETHASONE | 25.2 ± 1.6 | 33.2 ± 1.3 | 1.3 ± 0.1 | 46.3 ± 2.5 | 1.9 ± 0.1 |
| 10 MG/KG DHEA | 23.7 ± 1.0 | 31.7 ± 2.6 | 1.3 ± 0.2 | 46.4 ± 3.7 | 2.0 ± 0.2 |
| 20 MG/KG DHEA | 24.5 ± 2.1 | 36.6 ± 5.2 | 1.5 ± 0.2 | 51.4 ± 2.2 | 2.1 ± 0.2 |
| 10 MG/KG FLUASTERONE | 24.3 ± 1.0 | 60.9 ± 5.2 | 2.5 ± 0.3 | 77.5 ± 14.4 | 3.2 ± 0.5 |
| 20 MG/KG FLUASTERONE | 25.2 ± 0.6 | 60.8 ± 5.3 | 2.4 ± 0.2 | 73.9 ± 13.8 | 2.9 ± 0.6 |

The data indicate that DHEA, at a dose of 20 mg/kg, produces no apparent protection against dexamethasone-induced thymic or splenic atrophy. But surprisingly, fluasterone is highly active in protecting thymus and spleen at a dose of 10 mg/kg.

Example 8

Comparison Between Micronized DHEA and Micronized Fluasterone

The dexamethasone induced thymic and splenic atrophy experiments were performed using procedures similar to those set forth above.

TABLE 13

Average body weight of mice before the experiment

| Control | Dexa-methasone | 20 mg/kg DHEA | 60 mg/kg DHEA | 10 mg/kg Fluasterone | 20 mg/kg Fluasterone |
|---|---|---|---|---|---|
| 26.1 ± 1.2 | 26.4 ± 1.6 | 26.1 ± 3.4 | 26.4 ± 3.3 | 26.7 ± 3.6 | 26.4 ± 3.5 |

TABLE 14

Average mouse thymus and spleen weights after euthanization

| Group | Body Weight | Thymus wt | Thymus wt/BW | Spleen wt | Spleen wt/BW |
|---|---|---|---|---|---|
| CONTROL | 26.6 ± 2.8 | 71.5 ± 7.0 | 2.7 ± 0.3 | 91.1 ± 11.3 | 3.4 ± 0.1 |
| DEXAMETHASONE | 27.3 ± 1 | 35.7 ± 3.8 | 1.3 ± 0.1 | 47.8 ± 3.3 | 1.7 ± 0.1 |
| 20 MG/KG DHEA | 27.4 ± 4.0 | 39.3 ± 4.1 | 1.4 ± 0.1 | 56.8 ± 8.1 | 2.1 ± 0.1 |
| 60 MG/KG DHEA | 27.0 ± 3.1 | 63.2 ± 7.8 | 2.3 ± 0.2 | 79.9 ± 16.0 | 3.0 ± 0.4 |
| 10 MG/KG FLUASTERONE | 26.7 ± 3.6 | 68.0 ± 11.5* | 2.5 ± 0.3 | 83.0 ± 6.2** | 3.1 ± 0.3 |
| 20 MG/KG FLUASTERONE | 27.2 ± 3.1 | 66.3 ± 9.0** | 2.4 ± 0.2 | 83.1 ± 7.9* | 3.1 ± 0.4 |

*$p < 0.01$, versus 20 mg/kg DHEA group.
**$p < 0.001$, versus 20 mg/kg DHEA group.

The data indicate that fluasterone is about 6× as potent as DHEA in protecting against dexamethasone-induced thymic and splenic atrophy.

Example 9

Comparison of 30-methyl-16α-fluoro-5-androsten-17-one, 16α-methyl-5-androsten-17-one, 30β-methyl-5-androsten-17-one, 3β-methyl-16α-methyl-5-androsten-17-one and 3β-methyl-16α-chloro-5-androsten-17-one with fluasterone and DHEA for Anti-Atrophic Activity The dexamethasone induced thymic and splenic atrophy experiments were performed using procedures similar to those set forth above for a series of compounds of formula I.

Formulations containing one of the compounds of formula I, 16α-fluoro-5-androsten-17-one (Fluasterone), 3β-methyl-16α-fluoro-5-androsten-17-one, 16α-methyl-5-androsten-17-one, 3β-methyl-5-androsten-17-one and, 3β-methyl-16α-chloro-5-androsten-17-one, 7α-hydroxy-16α-fluoro-5-androsten-17-one (7α-hydroxy-fluasterone) and 3β-methyl-16α-methyl-5-androsten-17-one were prepared as described below.

Fluasterone (10 mg/kg) suspension: For the 10 mg/kg Fluasterone suspension, 35.4 mg non-micronized Fluasterone was weighed out, transferred to a glass scintillation vial, and 14.1 mL of Cremophor-saline vehicle was added. The suspension was homogenized using a Tissumizer at 80% power for 30 sec. The Tissumizer was rinsed with 70% ethanol prior to homogenization.

The probe was then washed with detergent, rinsed with 500 mL deionized water, 5×, rinsed with 70% ethanol, and then the probe was dried with a sterile gauze pad prior to homogenizing the 10 mg/kg 3β-methyl-16α-fluoro-5-androsten-17-one suspension.

3β-methyl-16α-fluoro-5-androsten-17-one suspensions: For the 10 mg/kg suspension, 11 mg of 3β-methyl-16α-fluoro-5-androsten-17-one was weighed out and transferred to a 7 mL plastic vial. 11 mL of Cremophor-saline vehicle was added to the vial and the contents of the vial were homogenized with a Tissumizer as described previously. Prior to preparing the 20 mg/kg 3β-methyl-16α-fluoro-5-androsten-17-one suspension, the probe was rinsed 2× with 50 mL of absolute ethanol and 1× with 50 mL of 70% ethanol. For the 20 mg/kg suspension, 16.9 mg was weighed out and transferred to a 7 mL plastic vial. 3.4 mL of Cremophor-saline vehicle was added to the vial and the contents of the vial were homogenized with a Tissumizer as described above.

16α-methyl-5-androsten-17-one (10 mg/kg) suspension: The 10 mg/kg suspension was prepared by weighing out 11.2 mg transferring to a 7 mL plastic vial, and adding 4.5 mL of vehicle. The suspension was homogenized as described previously.

3β-methyl-16α-chloro-5-androsten-17-one suspensions: For the 10 mg/kg suspension, 8.3 mg of 3β-methyl-16α-chloro-5-androsten-17-one was weighed out, transferred to a 7 mL plastic vial, and 3.3 mL of Cremophor-saline vehicle was added. For the 20 mg/kg suspension, 17.4 mg was weighed out, transferred to a 7 mL plastic vial, and 3.5 mL of vehicle was added to the vial. The suspensions were homogenized as described previously.

3β-methyl-5-androsten-17-one suspensions The 10 mg/kg suspension was prepared by weighing out 18.5 mg of 3β-methyl-5-androsten-17-one, transferring to a 7 mL plastic vial, and adding 7.4 mL of vehicle. For the 20 mg/kg suspension, 31 mg was weighed out and 6.2 mL of vehicle was added to the vial.

3β-methyl-16α-methyl-5-androsten-17-one suspensions The 10 mg/kg suspension was prepared by weighing out 20.0 mg suspension, transferring to a vial, and adding 8 mL of vehicle. For the 20 mg/kg suspension, 35.2 mg was weighed out and added 7.0 mL of vehicle to the vial.

Mice: Female CD-1 mice, 44-46 days old, were obtained from Charles River Laboratories. Prior to the experiments the mice were housed 5 per cage in plastic shoebox cages with ad libitum access to Purina chow 5015 and water in the Pharmacy CAF with 12 hr of alternating light and darkness.

Two mice in the 20 mg/kg 3β-methyl-16α-methyl-5-androsten-17-one group never recovered from anesthesia. The other three mice in this group came out of anesthesia very slowly.

Mice were treated with specific steroids and dexamethasone-induced thymic and splenic atrophy procedures were performed as set forth above.

TABLE 15

Average thymus and spleen weights of mice after euthanization

| Group | Body Weight | Thymus wt | Thymus wt/BW | Spleen wt | Spleen wt/BW |
|---|---|---|---|---|---|
| CONTROL | 25.9 ± 1.1 | 83.2 ± 6.6 | 3.2 ± 0.3 | 98.5 ± 9.7 | 3.8 ± 0.3 |
| DEXAMETHASONE | 25.2 ± 0.9 | 36.0 ± 4.9 | 1.4 ± 0.2 | 47.2 ± 6.1 | 1.9 ± 0.2 |
| 10 MG/KG FLUASTERONE | 24.8 ± 0.8 | 67.5 ± 3.9 | 2.7 ± 0.2 | 80.0 ± 7.7 | 3.2 ± 0.4 |
| 10 mg/kg 3β-methyl-16α-fluoro-5-androsten-17-one | 25.5 ± 0.7 | 43.8 ± 3.0 | 1.7 ± 0.1 | 50.9 ± 7.5 | 2.0 ± 0.3 |
| 20 mg/kg 3β-methyl-16α-fluoro-5-androsten-17-one | 25.5 ± 0.9 | 55.8 ± 5.4 | 2.2 ± 0.2 | 55.0 ± 4.6 | 2.2 ± 0.1 |
| 10 mg/kg 16α-methyl-5-androsten-17-one | 25.3 ± 0.8 | 28.0 ± 1.7 | 1.1 ± 0.1 | 37.8 ± 6.1 | 1.5 ± 0.3 |
| 10 mg/kg 3β-methyl-5-androsten-17-one | 24.2 + 1.1 | 61.9 + 3.9 | 2.6 + 0.2 | 70.7 + 4.5 | 2.9 + 0.2 |
| 20 mg/kg 3β-methyl-5-androsten-17-one | 25.8 ± 2.6 | 62.2 ± 4.1 | 2.4 ± 0.2 | 67.0 ± 11.3 | 2.6 ± 0.2 |
| 10 mg/kg 3β-methyl-16α-methyl-5-androsten-17-one | 25.8 ± 0.6 | 42.6 + 4.7 | 1.7 + 0.2 | 44.9 + 9.2 | 1.7 + 0.3 |
| 20 mg/kg 3β-methyl-16α-methyl-5-androsten-17-one | 25.3 ± 1.6 | 37.7 ± 4.0 | 1.5 ± 0.2 | 44.4 ± 8.7 | 1.8 ± 0.3 |
| 10 mg/kg 3β-methyl-16α-chloro-5-androsten-17-one | 26.0 ± 1.9 | 31.7 ± 4.1 | 1.2 ± 0.1 | 42.3 ± 5.6 | 1.6 ± 0.2 |
| 20 mg/kg 3β-methyl-16α-chloro-5-androsten-17-one | 26.4 ± 0.7 | 28.6 ± 3.2 | 1.1 ± 0.1 | 38.6 ± 6.3 | 1.2 ± 0.3 |

The data indicate that fluasterone is the most potent compound in protecting against dexamethasone-induced thymic and splenic atrophy.

Example 10

Comparison of 16α-fluoro-5α-androstan-17-one (8356), 7α-hydroxyfluasterone, 16α-fluoro-5-androsten-17-ol, 16α-hydroxy-5-androsten-17-one with Fluasterone and DHEA for Anti-Atrophic Activity The activity of title compounds against dexamethasone-induced thymic and spleen atrophy was tested in procedures analogous to those described above, and the results are given in Table 15.

TABLE 16

Average thymus and spleen weights of mice after euthanization

| Group | Body Weight | Thymus wt | Thymus wt/BW | Spleen wt | Spleen wt/BW |
|---|---|---|---|---|---|
| CONTROL | 25.6 ± 1.0 | 78.8 ± 11.2 | 3.1 ± 0.4 | 85.8 ± 20.1 | 3.3 ± 0.7 |
| DEXAMETHASONE | 24.7 ± 1.2 | 27.3 ± 3.3 | 1.1 ± 0.2 | 42.8 ± 4.6 | 1.7 ± 0.2 |
| 20 MG/KG 8356 | 25.2 ± 2.9 | 40.8 ± 5.8 | 1.6 ± 0.1 | 54.0 ± 4.5 | 2.0 ± 0.3 |
| 40 MG/KG 8356 | 25.2 ± 1.4 | 54.4 ± 4.5 | 2.2 ± 0.2 | 51.2 ± 3.0 | 2.0 ± 0.2 |
| 5 MG/KG FLUASTERONE | 25.7 ± 1.7 | 50.8 ± 10.9 | 2.0 ± 0.3 | 62.0 ± 10.2 | 2.4 ± 0.3 |
| 10 MG/KG FLUASTERONE | 25.2 ± 1.4 | 65.6 ± 4.4 | 2.6 ± 0.2 | 89.4 ± 12.3 | 3.5 ± 0.4 |
| 5 mg/kg 7α-hydroxyfluasterone | 24.5 ± 1.0 | 43.8 ± 6.9 | 1.8 ± 0.3 | 46.3 ± 11.1 | 1.8 ± 0.5 |
| 10 mg/kg 7α-hydroxyfluasterone | 24.0 ± 1.3 | 54.8 ± 12.1 | 2.3 ± 0.4 | 50.9 ± 12.5 | 2.1 ± 0.5 |

TABLE 16-continued

Average thymus and spleen weights of mice after euthanization

| Group | Body Weight | Thymus wt | Thymus wt/BW | Spleen wt | Spleen wt/BW |
|---|---|---|---|---|---|
| 20 mg/kg 16α-fluoro-5-androsten-17-ol | 25.1 ± 1.0 | 42.3 ± 4.6 | 1.7 ± 0.2 | 52.3 ± 10.8 | 2.1 ± 0.4 |
| 60 mg/kg 16α-fluoro-5-androsten-17-ol | 25.7 ± 1.5 | 45.1 ± 5.1 | 1.8 ± 0.2 | 45.9 ± 5.1 | 1.8 ± 0.2 |
| 20 mg/kg 16α-hydroxy-5-androsten-17-one | 25.4 ± 1.5 | 41.2 ± 1.3 | 1.6 ± 0.1 | 46.6 ± 7.5 | 1.8 ± 0.2 |
| 60 mg/kg 16α-hydroxy-5-androsten-17-one | 23.8 ± 0.8 | 45.9 ± 3.1 | 1.9 ± 0.2 | 53.6 ± 6.3 | 2.2 ± 0.3 |

Example 11

Gel Compositions with Fluasterone

A gel can be formed upon the addition of small amounts of water (about 5%) to 10 mg/mL solutions of fluasterone in Tween 80:ethanol. However, substantial fluasterone precipitation occurred. An attempt was made to form a gel by adding carbomer to mixtures of ethanol and various organic solvents without water, and this was unsuccessful.

A gel containing fluasterone was made using a suspension of micronized fluasterone. This suspension of fluasterone was about as effective as s.c.-injection in abolishing TPA-stimulated DNA synthesis in mouse.

Fluasterone:Ethanol:Water:Tween Gel
The following were added to a screw cap glass scintillation vial:
7.5 mL absolute ethanol (PharmCo, ACS/USP Grade)
2.5 mL double distilled water
0.5 mL Tween 80 (Sigma, ultra pure)
97.1 mg of micronized fluasterone was added to the above and the suspension was sonicated with a Tekmar Tissumizer for about one minute at high speed. 60 mg Carbomer 940 (Spectrum Chem.) was added to the suspension and shook vigorously for several minutes, followed by the addition of 10 μL of triethanolamine (Sigma. Suspension turned into a gel after overnight incubation at room temperature. The gel was easy to apply and disappeared quickly from the skin.

Example 12

Micronized Fluasterone

A 450 gm sample of unmilled fluasterone (19.33 μm) was processed through an air jet pulverizer mill at 90 psi at rate of 6 kg/hr. The resulting milled fluasterone had a mean particle size of 6.16 μm (Micronized I; MI).

A 350 gm of unmilled fluasterone was processed through an air-jet pulverizer at 90 psi at a reduced rate of 0.60 kg/hr, resulting in finer particles. This procedure produced a milled fluasterone product with a mean particle size of 2.04 μm. (Micronized II; MII)

Reducing fluasterone mean particle size from 19.33 to 6.16 μm enhanced oral bioavailability, and reducing particle size to 2.04 μm further improved oral bioavailability.

Determination of Oral Bioavailability of Micronized Fluasterone:
Treatment of Mice: Mice CD-1 mice (42-45 days old) were obtained from Charles River Laboratories, Kingston, N.Y. The mice were housed three per cage in plastic shoebox cages on corncob bedding at 72°±2° F. with 50%±5% humidity and 12 hours of alternating light and dark in the Fels Animal Facility. The mice had ad libitum access to Purina 5015 chow and acidified tap water (pH≦2.6). The mice were allowed to acclimate to the facility for one week prior to use in an experiment.

102.7 mg of Micronized fluasterone I was weighed using a Mettler AE-50 balance, transferred to a glass scintillation vial, and homogenized in 6.0 mL of carboxymethylcellulose-Tween 80 using a Tekmar Tissumizer (200 mg/kg micronized I suspension, 200 MI). 88.4 mg of micronized fluasterone II was then weighed, transferred to a glass scintillation vial, and homogenized in 5.2 mL of CMC-Tween using a Tekmar Tissumizer (200 mg/kg micronized II suspension, 200 MII). 179.2 mg of micronized fluasterone II was weighed, transferred to a glass scintillation vial, and homogenized in 5.2 mL of CMC-Tween (400 mg/kg micronized II suspension, 400 MII). 93.0 mg of non-micronized fluasterone (mean particle size, 19.92 μm) was weighed, transferred to a glass scintillation vial, and homogenized in 5.5 mL of CMC-Tween (200 mg/kg non-micronized suspension, 200 R). 167.0 mg of non-micronized fluasterone was weighed, transferred to a glass scintillation vial, and homogenized in 4.9 mL of CMC-Tween (400 mg/kg non-micronized suspension, 400 R). 261.5 mg of non-micronized fluasterone was weighed, transferred to a glass scintillation vial, and homogenized in 5.1 mL of CMC-Tween (600 mg/kg non-micronized suspension, 600 R). A magnetic stirrer was added to each of the vials and the suspensions were stirred for approximately 45 minutes prior to intubation. The mice were intubated using 18 gauge stainless steel intubating needles.

The mice were treated as follows:
Control were intubated with 0.25 ml of CMC-Tween. One hour after intubation with CMC-Tween, the mice were treated with 0.2 mL of acetone. The mice were given ad libitum access to chow immediately after intubation.

TPA were intubated with 0.25 ml of CMC-Tween. One hour after intubation with CMC-Tween, the mice were treated with 2 μg of TPA in 0.2 mL of acetone. The mice were given ad libitum access to chow immediately after intubation.

600 R were intubated with 0.25 ml of a 600 mg/kg suspension of non-micronized fluasterone. One hour after intubation with CMC-Tween, the mice were treated with 2 μg of TPA in 0.2 mL of acetone. The mice were given ad libitum access to chow immediately after intubation.

400 R were intubated with 0.25 ml of a 400 mg/kg suspension of non-micronized fluasterone. One hour after intubation with CMC-Tween, the mice were treated with 2 μg of TPA in 0.2 mL of acetone. The mice were given ad libitum access to chow immediately after intubation.

200 R were intubated with 0.25 ml of a 20 mg/kg suspension of non-micronized fluasterone. One hour after intubation with CMC-Tween, the mice were treated with 2 μg of TPA in 0.2 mL of acetone. The mice were given ad libitum access to chow immediately after intubation.

400 MII were intubated with 0.25 ml of a 400 mg/kg suspension of micronized fluasterone II in CMC-Tween. One hour after intubation with CMC-Tween, the mice were treated with 2 μg of TPA in 0.2 mL of acetone. The mice were given ad libitum access to chow immediately after intubation.
200 MII were intubated with 0.25 ml of a 200 mg/kg suspension of micronized fluasterone II in CMC-Tween. One hour after intubation with CMC-Tween, the mice were treated with 2 μg of TPA in 0.2 mL of acetone. The mice were given ad libitum access to chow immediately after intubation.
200 MI were intubated with 0.25 ml of a 200 mg/kg suspension of micronized fluasterone I in CMC-Tween. One hour after intubation with CMC-Tween, the mice were treated with 2 μg of TPA in 0.2 mL of acetone. The mice were given ad libitum access to chow immediately after intubation.

All mice started to consume chow immediately after the chow was added to cage.

The mice were sacrificed 20 hours after treatment by an overdose of $CO_2$. Twenty minutes prior to sacrifice, the mice were injected with 60 μCi of [3H]thymidine (Amersham). The mice were treated with a depilatory to remove any residual hair. A 2×2 cm piece of skin was excised, placed in ice water for 30 seconds, then in 55° water for 30 seconds, then in ice water again for 30 seconds. The epidermis was scraped off using a scalpel and the scrapings were placed into ice cold 0.4N TCA. The scrapings were homogenized using a Tekmar Tissumizer (80% power for 30 seconds). The homogenates were centrifuged for 20 minutes at 3000×g. The precipitates were washed 4× with 0.2N TCA, and 2× with absolute ethanol. The DNA was hydrolyzed with 0.5N TCA for 30 minutes at 90°. The tubes were centrifuged for 20 minutes at 3000×g. A 0.2 ml aliquot of each hydrolysate was counted in a LKB Rackbeta scintillation counter using Scintiverse II as the counting medium. DNA content was determined by the Burton diphenylamine assay.

TABLE 17

Average Body Weights

| Control | TPA | 600 R | 400 R | 200 R | 400 MII | 200 MII | 200 MI |
|---|---|---|---|---|---|---|---|
| 21.3 ± 0.4 | 21.4 ± 0.5 | 21.3 ± 0.3 | 21.2 ± 0.5 | 21.2 ± 0.4 | 21.5 ± 0.2 | 21.3 ± 0.3 | 21.3 ± 0.4 |

TABLE 18

Effect of Fluasterone on TPA-Induced Epidermal DNA Synthesis

| Group | corrected cpm | μg DNA/0.2 ml | cpm/μg DNA |
|---|---|---|---|
| Control | 1,900 | 16.4 | 115.9 |
|  | 2594 | 14.6 | 177.7 |
|  | 1494 | 18.0 | 83.0 |
|  |  |  | 125.5 ± 48.1 |
| TPA | 8,699 | 28.2 | 308.5 |
|  | 9,877 | 28.0 | 351.6 |
|  | 8,235 | 31.9 | 258.6 |
|  |  |  | 306.1 ± 46.8 |
| 600 R | 2,343 | 17.9 | 130.9 |
| 600 mg/kg | 2,346 | 17.3 | 135.6 |
| NON-MICRONIZED | 2,732 | 16.5 | 165.6 |
|  |  |  | 144.0 ± 18.8 |
| 400 R | 3,479 | 21.4 | 162.9 |
| 400 mg/kg | 4,101 | 18.2 | 225.3 |
| NON-MICRONIZED | 3,358 | 19.7 | 170.4 |
|  |  |  | 186.1 ± 34.2 |
| 200 R | 5,120 | 20.0 | 256.0 |
| 200 mg/kg | 7,807 | 18.0 | 433.7 |
| NON-MICRONIZED | 5,365 | 19.7 | 257.9 |
|  |  |  | 315.9 ± 102.1 |
| 400 MII | 1,941 | 16.5 | 117.6 |
| 400 mg/kg | 2,136 | 17.2 | 120.7 |
| MICRONIZED II | 1,138 | 17.7 | 120.8 |
|  |  |  | 119.7 ± 1.8 |
| 200 MII | 2,666 | 16.0 | 166.6 |
| 200 mg/kg | 2,856 | 23.1 | 123.6 |
| MICRONIZED II | 2,753 | 22.9 | 120.2 |
|  |  |  | 136.8 ± 25.9 |

TABLE 18-continued

Effect of Fluasterone on TPA-Induced Epidermal DNA Synthesis

| Group | corrected cpm | μg DNA/0.2 ml | cpm/μg DNA |
|---|---|---|---|
| 200 MI | 2,763 | 17.7 | 156.1 |
| 200 mg/kg | 3,554 | 24.4 | 145.7 |
| MICRONIZED I | 3,563 | 23.5 | 151.6 |
| (first prep) |  |  | 151.1 ± 5.2 |

The Micronized I sample (6.16 μm) was about 2 to 3-fold more potent than the Non-micronized sample (19.33 μm), and the Micronized II sample (2.14 μm) was more potent than Micronized I.

Example 13

Effect of Orally Administered Micronized Fluasterone and Nanosized Fluasterone on TPA-Induced Epidermal DNA Synthesis in Mice In this experiment nanosized fluasterone (mean particle size=0.621 μm) was compared to micronized fluasterone (mean particle size 5.5 μm) for efficacy in suppressing TPA-stimulated epidermal DNA synthesis in mouse skin. Both preparations were administered as suspensions in an aqueous vehicle at p.o. dosages of 200 mg/kg, 150 mg/kg, and 100 mg/kg.

Mice were given an oral intubation of 0.2 ml sesame oil ten minutes prior to dosing with fluasterone in aqueous suspension. In prior experiments we found that either dosing with 0.2 ml sesame oil or allowing the mice to consume food shortly before administering fluasterone in an aqueous vehicle enhances bioavailability. Presumably this had the same effect (i.e. bile salt release) as food given to patients as shown in the phase I study.

The nanosized fluasterone suspension is the most active formulation we have tested to date and would appear to be about 2× as bioavailable as the 5.5 μm suspension.
Methods and Experimental Results Female CD-1 mice were obtained from Charles River Laboratories, Wilmington, Mass. at 46-48 days of age. The mice were housed three per cage in plastic shoebox cages on Aspen chip bedding with 12 hours of alternating light and dark in the Fels Animal Facility. The mice had ad libitum access to Purina 5015 chow and acidified tap water (pH #2.6). The mice were allowed to acclimate to the facility for one week prior to use in an experiment. Three days later the mice were shaved.

The concentration of the micronized fluasterone suspension was 155.4 mg/g of suspension while that of the nanosized fluasterone suspension was 109.5 mg/g of suspension. A gram of the micronized suspension was equal to 1.02 ml, while that of the nanosized suspension was assumed to be 1 g/ml.

Five suspensions were prepared approximately one-half hour prior to treatment. 354 μL (53.9 mg) of micronized fluasterone was added to 1,646 μL of vehicle to give a suspension yielding a dose of 200 mg/kg when given p.o. at 0.2 mL (26.9 mg/ml). 263 μL of micronized suspension (40.1 mg) was added to 1,737 μL of vehicle to give a suspension yielding 150 mg/kg (20.0 mg/ml). For the nanosized suspensions: 473 µL (51.8 mg) was added to 1,527 µL of vehicle to give a suspension yielding 200 mg/kg (25.9 mg/ml), 360 µL (39.4 mg) of nanosized fluasterone suspension was added to 1,640 µL of vehicle to give a suspension yielding 150 mg/kg (19.7 mg/ml), 300 µL (32.9 mg) was added to 1,700 µL of vehicle to give a suspension yielding 125 mg/kg (16.6 mg/ml) and 230 µL (25.2 mg) was added to 1,770 µL of vehicle to give a suspension yielding 100 mg/kg (12.6 mg/ml). A magnetic stirrer was added to each of the vials and the suspensions were stirred without heat.

The mice were treated as follows:

Control The mice were given 0.2 ml of sesame oil p.o, and ten minutes later, were treated with 0.2 ml of suspension vehicle p.o. One hour after treatment with the vehicle, the mice were treated topically with 0.2 ml of acetone.

TPA The mice were given 0.2 ml of sesame oil p.o, and ten minutes later, were treated with 0.2 ml of suspension vehicle p.o. One hour after treatment with the vehicle, the mice were treated topically with 2 µg of TPA dissolved in 0.2 ml of acetone.

200 mg/kg Fluasterone Micronized
The mice were treated 0.2 ml of sesame oil p.o. ten minutes prior to treatment p.o. with 0.2 ml of a suspension of micronized fluasterone which gave a dose of 200 mg/kg. One hour after treatment with the micronized fluasterone suspension, the mice were treated topically with 2 µg of TPA dissolved in 0.2 ml of acetone.

150 mu/kg Fluasterone Micronized The mice were treated 0.2 ml of sesame oil p.o. ten minutes prior to treatment p.o. with 0.2 ml of a suspension of micronized fluasterone which gave a dose of 150 mg/kg. One hour after treatment with the micronized fluasterone suspension, the mice were treated topically with 2 µg of TPA dissolved in 0.2 ml of acetone.

200 mu/kg Fluasterone Nanosized The mice were treated 0.2 ml of sesame oil p.o. ten minutes prior to treatment p.o. with 0.2 ml of a suspension of nanosized fluasterone which gave a dose of 200 mg/kg. One hour after treatment with the nanosized fluasterone suspension, the mice were treated topically with 2 µg of TPA dissolved in 0.2 ml of acetone.

200 mu/kg Fluasterone Nanosized The mice were treated 0.2 ml of sesame oil p.o. ten minutes prior to treatment p.o. with 0.2 ml of a suspension of nanosized fluasterone which gave a dose of 150 mg/kg. One hour after treatment with the nanosized fluasterone suspension, the mice were treated topically with 2 µg of TPA dissolved in 0.2 ml of acetone.

125 mu/kg Fluasterone Nanosized The mice were treated 0.2 ml of sesame oil p.o. ten minutes prior to treatment p.o. with 0.2 ml of a suspension of nanosized fluasterone which gave a dose of 150 mg/kg. One hour after treatment with the nanosized fluasterone suspension, the mice were treated topically with 2 µg of TPA dissolved in 0.2 ml of acetone.

100 mu/kg Fluasterone Nanosized The mice were treated 0.2 ml of sesame oil p.o. ten minutes prior to treatment p.o. with 0.2 ml of a suspension of nanosized fluasterone which gave a dose of 100 mg/kg. One hour after treatment with the nanosized fluasterone suspension, the mice were treated topically with 2 µg of TPA dissolved in 0.2 ml of acetone.

The mice were sacrificed 20 hours after treatment by an overdose of $CO_2$. Twenty minutes prior to sacrifice, the mice were injected with 60 µCi of [$^3$H]thymidine (Amersham). The mice were treated with a depilatory to remove any residual hair. A 2×2 $cm^2$ piece of skin was excised, placed in ice water for 30 seconds, then in 55EC water for 30 seconds, then in ice water again for 30 seconds. The epidermis was scraped off using a scalpel and the scrapings were placed into ice cold 0.4N TCA. The scrapings were homogenized using a Tekmar Tissumizer (80% power for 30 seconds). The homogenates were centrifuged for 20 minutes at 3,000×g. The precipitates were washed 4× with 0.2N TCA, and 2× with absolute ethanol. The DNA in each sample was hydrolyzed with 0.5N TCA for 30 minutes at 90E. The tubes were centrifuged for 20 minutes at 3000×g. A 0.2 ml aliquot of each hydrolysate was counted in a LKB Rackbeta scintillation counter using Scintiverse II BD as the counting medium. DNA content was determined by the Burton diphenylamine assay.

TABLE 19

| | | Body Weights | | | | | |
|---|---|---|---|---|---|---|---|
| Control | TPA | 200 mg/kg micronized | 150 mg/kg micronized | 200 mg/kg nanosized | 150 mg/kg nanosized | 125 mg/kg nanosized | 100 mg/kg nanosized |
| 26.0 ± 1.9 | 26.8 ± 3.4 | 26.9 ± 1.5 | 26.7 ± 2.1 | 25.9 ± 1.6 | 26.2 ± 1.6 | 26.5 ± 1.2 | 25.2 ± 1.0 |

TABLE 20

Results: Effect of oral intake of micronized and nanosized fluasterone

| Group | µg DNA | cpm/µg DNA | dpm/µg DNA |
|---|---|---|---|
| Control | 8.0 ± 0.9 | 161.4 ± 9.6 | 260.4 ± 15.5 |
| TPA | 13.9 ± 0.3 | 374.1 ± 16.8 | 603.4 ± 36.8 |
| Micronized 200 mg/kg | 7.0 ± 0.3 | 163.9 ± 26.1 | 264.4 ± 42.1 |
| Micronized 150 mg/kg | 14.4 ± 0.5 | 479.3 ± 41.5 | 773.1 ± 66.8 |
| Nanosized 200 mg/kg | 8.1 ± 0.8 | 102.2 ± 26.7 | 164.7 ± 43.0 |
| Nanosized 150 mg/kg | 6.9 ± 0.3 | 123.5 ± 10.6 | 199.3 ± 17.1 |
| Nanosized 125 mg/kg | 7.1 ± 0.4 | 125.0 ± 29.7 | 201.6 ± 47.9 |
| Nanosized 100 mg/kg | 8.9 ± 0.6 | 187.4 ± 41.1 | 302.2 ± 66.2 |

While this invention has been particularly shown and described with references to preferred embodiments thereof, it will be understood by those skilled in the art that various changes in form and details may be made therein without departing from the scope of the invention encompassed by the appended claims.

What is claimed is:

1. A pharmaceutical composition comprising a suspension comprising a nanosized compound selected from the group consisting of 3β-methyl-5-androsten-17-one, 3β-methyl-16α-fluoro-5-androsten-17-one and 16α-fluoro-5-androsten-17-one; a lower alkyl alcohol; a surfactant; and optionally, a long chain alcohol.

2. A composition according to claim 1, wherein said long chain alcohol corresponds to the formula $CH_3(CH_2)_n$—OH, wherein n is an integer in the range of 9-24.

3. A composition according to claim 2, wherein said long chain alcohol is selected from the group consisting of decyl alcohol, cetyl alcohol, stearyl alcohol, lauryl alcohol, myristyl alcohol, oleyl alcohol and mixtures thereof.

4. A composition according to claim 1, further comprising water.

5. A transdermal delivery system comprising a composition of claim 1.

6. A topical formulation comprising a composition of claim 1.

7. A method for the treatment of obesity, type II diabetes, arthritis or metabolic syndrome in a patient in need thereof, which comprises administering to said patient a therapeutically effective amount of a composition of claim 1.

8. The method according to claim 7, wherein said treatment is for type II diabetes.

9. The method according to claim 7, wherein the treatment is for obesity.

10. A gel comprising a nanosized compound selected from the group consisting of 3β-methyl-5-androsten-17-one, 3β-methyl-16α-fluoro-5-androsten-17-one and 16α-fluoro-5-androsten-17-one; a lower alkyl alcohol; water; a surfactant; a thickening agent; and optionally a base.

11. The gel according to claim 10, wherein said lower alkyl alcohol is selected from the group consisting of ethanol, methanol, butanol, pentanol, isopropanol and n-propanol.

12. The gel according to claim 10, wherein said base is selected from the group consisting of triethanolamine, diethanolamine and triethylamine.

13. A method of preparing a gel comprising a nanosized compound selected from the group consisting of 3β-methyl-5-androsten-17-one, 3β-methyl-16α-fluoro-5-androsten-17-one and 16α-fluoro-5-androsten-17-one, comprising the steps of: mixing a lower alkyl alcohol, a surfactant, a base, water and said nanosized compound; adding and mixing a cross-linked acrylic acid polymer; and incubating said ingredients until gel formation.

14. A method of treating cancer comprising administering to a subject in need thereof a composition of claim 1.

15. The method of claim 14, wherein said cancer is prostate cancer.

16. The gel according to claim 10 wherein the surfactant is a polysorbate.

17. The gel according to claim 16 which comprises:
from about 30 to about 90% (v/v) lower alcohol; and
from about 0.01 to about 5% (v/v) surfactant.

18. A method of treating diabetes comprising administering to a mammal in need thereof a composition according to claim 1.

19. The method according to claim 7, wherein said treatment is for arthritis.

20. A transdermal delivery system comprising a composition of claim 10.

21. A topical formulation comprising a composition of claim 10.

22. A method for the treatment of obesity, arthritis, type II diabetes or metabolic syndrome in a patient in need thereof, which comprises administering to said patient a therapeutically effective amount of a composition comprising a gel according to claim 10.

23. The method according to claim 22, wherein said treatment is for type II diabetes.

24. The method according to claim 22 wherein the treatment is for obesity.

25. The method according to claim 22, wherein the treatment is for rheumatoid arthritis or osteoarthritis.

26. The method according to claim 22, wherein said lower alkyl alcohol is selected from the group consisting of ethanol, methanol, butanol, pentanol, isopropanol and n-propanol.

27. The method according to claim 22 wherein the surfactant is a polysorbate.

28. The method according to claim 27, wherein said polysorbate is selected from the group consisting of polyoxyethylene-20-sorbitan monooleate (Tween 80), polyoxyethylene-20-sorbitan monostearate (Tween 60), polyoxyethylene-20-sorbitan monopalmitate (Tween 40), polyoxyethylene-20-sorbitan monolaurate (Tween 20), and mixtures thereof.

29. The method according to claim 13, wherein said cross-linked acrylic acid polymer is a Carbomer.

30. The composition of claim 1, wherein said nanosized compound is 16α-fluoro-5-androsten-17-one.

31. The method of claim 7 or 22, wherein said nanosized compound is 16α-fluoro-5-androsten-17-one.

32. The gel according to claim 1 wherein said nanosized compound is 16α-fluoro-5-androsten-17-one.

33. The method of preparing a gel according to claim 13 wherein the nanosized compound is 16α-fluoro-5-androsten-17-one.

34. The pharmaceutical composition according to claim 1 wherein said surfactant is a polysorbate or a polyethyleneglycol substituted fatty acid.

35. The pharmaceutical composition according to claim 34 wherein said polysorbate is polyoxyethylene-20-sorbitan monooleate (Tween 80), and wherein said pharmaceutical composition comprises a lower alkyl alcohol in the range of from about 30 to about 90% (v/v), polyoxyethylene-20-sorbitan monooleate (Tween 80) in the range of from about 0.01% to about 3.5% and water in the range of from about 0% to about 60%.

36. The method according to claim 14, wherein said cancer is a cancer of the mammary gland, skin, colon, liver or lymphatic system.

37. A composition according to claim 34, wherein said polysorbate is selected from the group consisting of polyoxyethylene-20-sorbitan monooleate (Tween 80), polyoxyethylene-20-sorbitan monostearate (Tween 60), polyoxyethylene-20-sorbitan monopalmitate (Tween 40), polyoxyethylene-20-sorbitan monolaurate (Tween 20), polyethyleneglycol stearate, polyethyleneglycol oleate and mixtures thereof.

38. The method according to claim 19, wherein the treatment is for rheumatoid arthritis or osteoarthritis.

39. The gel according to claim 16, wherein said polysorbate is selected from the group consisting of polyoxyethylene-20-sorbitan monooleate (Tween 80), polyoxyethylene-20-sorbitan monostearate (Tween 60), polyoxyethylene-20-sorbitan monopalmitate (Tween 40), polyoxyethylene-20-sorbitan monolaurate (Tween 20), and mixtures thereof.

* * * * *

UNITED STATES PATENT AND TRADEMARK OFFICE
CERTIFICATE OF CORRECTION

PATENT NO. : 8,431,555 B2
APPLICATION NO. : 12/494928
DATED : April 30, 2013
INVENTOR(S) : Schwartz et al.

Page 1 of 1

It is certified that error appears in the above-identified patent and that said Letters Patent is hereby corrected as shown below:

In the Specification:

Column 41:
Lines 40-44, "16α-fluoro-5-androsten-17-ol" should read --16α-fluoro-5-androsten-17β-ol--.

Column 43:
In Table 16-continued, the two occurrences of "16α-fluoro-5-androsten-17-ol" should read --l6α-fluoro-5-androsten-17β-ol"--.

In the Claims:

Column 50:
Line 18, "1" should read --10--.

Signed and Sealed this
Fourth Day of February, 2014

Michelle K. Lee
*Deputy Director of the United States Patent and Trademark Office*